United States Patent
Harada et al.

(10) Patent No.: US 7,579,132 B2
(45) Date of Patent: Aug. 25, 2009

(54) SALT SUITABLE FOR AN ACID GENERATOR AND A CHEMICALLY AMPLIFIED POSITIVE RESIST COMPOSITION CONTAINING THE SAME

(75) Inventors: Yukako Harada, Settsu (JP); Isao Yoshida, Ikeda (JP); Satoshi Yamaguchi, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 242 days.

(21) Appl. No.: 11/806,799

(22) Filed: Jun. 4, 2007

(65) Prior Publication Data

US 2008/0044738 A1 Feb. 21, 2008

(30) Foreign Application Priority Data

Jun. 9, 2006 (JP) .............................. 2006-160706

(51) Int. Cl.
*G03F 7/004* (2006.01)
*C07C 69/74* (2006.01)
*C07C 309/05* (2006.01)

(52) U.S. Cl. .................... 430/270.1; 430/905; 430/907; 430/910; 430/921; 430/922; 560/126; 562/109; 562/113

(58) Field of Classification Search .............. 430/270.1, 430/905, 907, 910, 921, 922; 560/126; 562/109, 562/113
See application file for complete search history.

(56) References Cited

U.S. PATENT DOCUMENTS

| 6,383,713 B1 | 5/2002 | Uetani et al. |
| 6,548,221 B2 | 4/2003 | Uetani et al. |
| 7,301,047 B2 * | 11/2007 | Yoshida et al. ............... 560/129 |
| 7,304,175 B2 * | 12/2007 | Harada et al. ................ 560/129 |
| 2003/0194639 A1 | 10/2003 | Miya et al. |
| 2007/0100158 A1 * | 5/2007 | Harada et al. ................ 560/149 |
| 2007/0100159 A1 * | 5/2007 | Yoshida et al. ............... 560/149 |
| 2007/0122750 A1 * | 5/2007 | Yamaguchi et al. ......... 430/311 |

FOREIGN PATENT DOCUMENTS

JP 2004-117959 A 4/2004

* cited by examiner

*Primary Examiner*—John S Chu
(74) *Attorney, Agent, or Firm*—Birch, Stewart, Kolasch & Birch, LLP

(57) ABSTRACT

The present invention provides a salt represented by the formula (I):

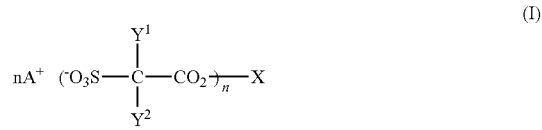

wherein X represents an n-valent connecting group, $Y^1$ and $Y^2$ each independently represent a fluorine atom or a C1-C6 perfluoroalkyl group, n represents 2 or 3, and $A^+$ represents an organic counter ion.

The present invention further provides a chemically amplified resist composition comprising the salt represented by the above-mentioned formula (I).

28 Claims, No Drawings

SALT SUITABLE FOR AN ACID GENERATOR AND A CHEMICALLY AMPLIFIED POSITIVE RESIST COMPOSITION CONTAINING THE SAME

This nonprovisional application claims priority under 35 U.S.C. § 119(a) on Patent Application No. 2006-160706 filed in JAPAN on Jun. 9, 2006, the entire contents of which are hereby incorporated by reference.

FIELD OF THE INVENTION

The present invention relates to a salt suitable for an acid generator used for a chemically amplified resist composition which is used in fine processing of semiconductors, and a chemically amplified positive resist composition containing the same.

BACKGROUND OF THE INVENTION

A chemically amplified positive resist composition used for semiconductor microfabrication employing a lithography process contains an acid generator comprising a compound generating an acid by irradiation.

In semiconductor microfabrication, it is desirable to form patterns having high resolution and excellent pattern shape, and it is expected for a chemically amplified resist composition to give such patterns.

U.S. Pat. No. 6,548,221 B2 and U.S. Pat. No. 6,383,713 B1 disclose a chemically amplified resist composition containing triphenylsulfonium perfluorobutanesulfonate as the acid generator.

JP 2004-4561 A also discloses a chemically amplified resist composition containing the salt represented by the following formulae:

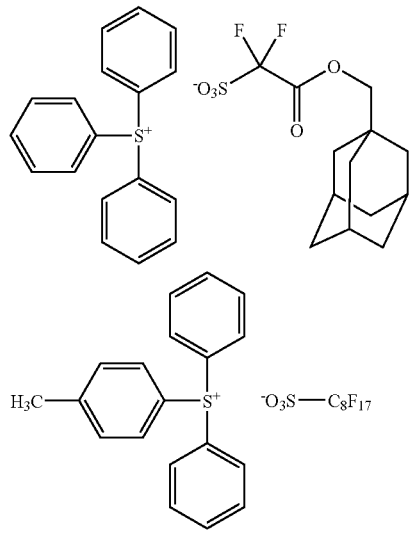

or the like as the acid generator.

SUMMARY OF THE INVENTION

An object of the present invention is to provide a salt suitable for an acid generator capable of providing chemically amplified resist compositionsgivingpattern-shavinghigh-resolutionandexcellentpattern shape.

Other objects of the present invention are to provide a synthetic intermediate for the salt and to provide a process for producing the synthetic intermediate or the salt.

Still another object of the present invention is to provide a chemically amplified resist composition containing the salt.

These and other objects of the present invention will be apparent from the following description.

The present invention relates to the followings:

<1> A salt-represented by the formula (I):

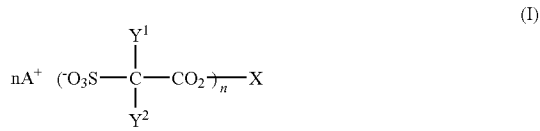

wherein X represents an n-valent connecting group, $Y^1$ and $Y^2$ each independently represent a fluorine atom or a C1-C6 perfluoroalkyl group, n represents 2 or 3, and $A^+$ represents an organic counter ion.

<2> The salt according to <1>, wherein $Y^1$ and $Y^2$ each independently represent a fluorine atom or a trifluoromethyl group.

<3> The salt according to <1> or <2>, wherein n is 2.

<4> The salt according to any one of <1> to <3>, wherein the organic counter ion is at least one cation selected from a cation represented by the formula (IIa):

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

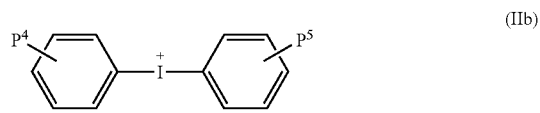

wherein $P^4$ and $P^5$ each independently represent a hydrogen atom, a hydroxyl group, a C1-C12 alkyl group or a C1-C12 alkoxy group, and a cation represented by the formula (IIc):

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —$CH_2$— in the divalent acyclic hydrocarbon group is optionally replaced with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ are bonded to form a divalent acyclic hydrocarbon group which forms a 2-oxocycloalkyl group together with the adjacent —CHCO—, and at least one —$CH_2$— in the divalent acyclic hydrocarbon group may be replaced with —CO—, —O— or —S—.

<5> The salt according to any one of <1> to <3>, wherein the organic counter ion is a cation represented by the formula (IId):

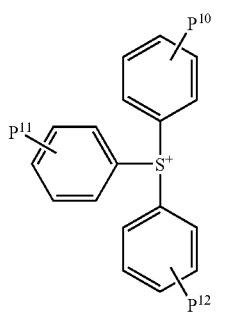

(IId)

wherein $P^{10}$, $P^{11}$ and $P^{12}$ each independently represent a hydrogen atom or a C1-C4 alkyl group.

<6> The salt according to any one of <1> to <5>, wherein the n-valent connecting group is a C1-C30 n-valent hydrocarbon group which may be substituted with at least one selected from a C1-C6 alkoxy group, a C1-C4 perfluoroalkyl group, a C1-C6 hydroxyalkyl group, a hydroxyl group and a cyano group, and at least one —$CH_2$— in the C1-C30 n-valent hydrocarbon group may be replaced with —O— or —CO—.

<7> The salt according to <1>, wherein the salt represented by the formula (I) is a salt represented by the formula (IIIa), (IIIb) or (IIIc);

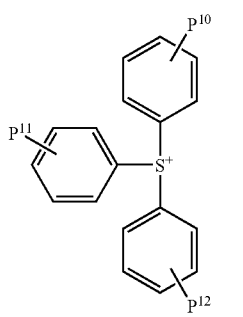

(IIIa)

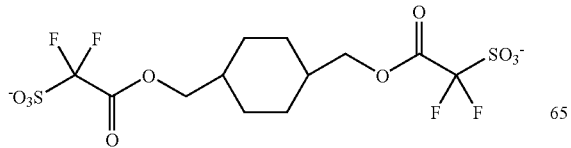

-continued

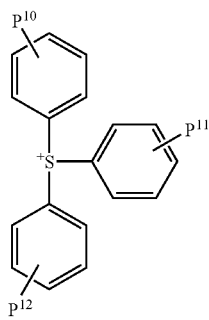

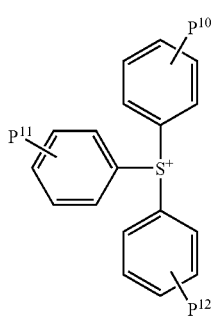

(IIIb)

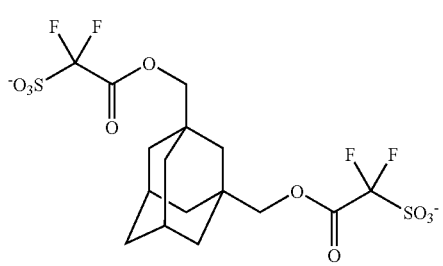

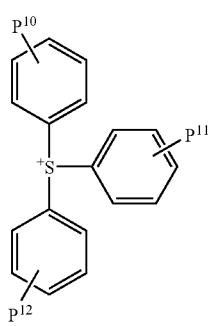

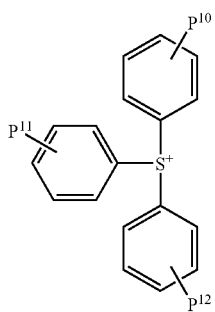

(IIIc)

-continued

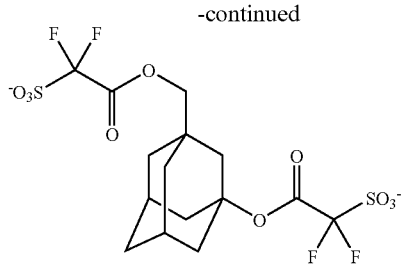

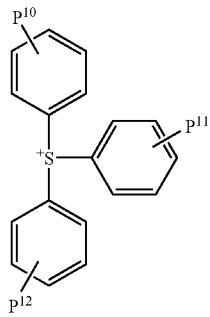

wherein $P^{10}$, $P^{11}$ and $P^{12}$ are the same as defined in claim 5.

<8> A salt represented by the formula (IV):

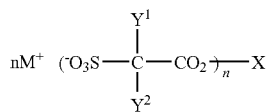
(IV)

wherein X represents an n-valent connecting group, $Y^1$ and $Y^2$ each independently represent a fluorine atom or a C1-C6 perfluoroalkyl group, n represents 2 or 3, and M represents Li, Na, K or Ag.

<9> A process for production of a salt represented by the formula (IV):

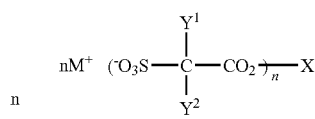
(IV)

wherein X represents an n-valent connecting group, $Y^1$ and $Y^2$ each independently represent a fluorine atom or a C1-C6 perfluoroalkyl group, n represents 2 or 3, and M represents Li, Na, K or Ag, which comprises reacting a compound represented by the formula (V):

(HO)$_n$X (V)

wherein X and n are the same as the defined above, with a salt represented by the formula (VI):

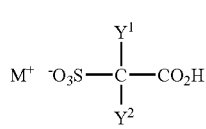
(VI)

wherein $Y^1$, $Y^2$ and M are the same as defined above.

<10> A process for production of a salt represented by the formula (IV):

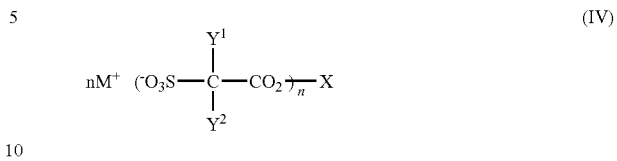
(IV)

wherein X represents an n-valent connecting group, $Y^1$ and $Y^2$ each independently represent a fluorine atom or a C1-C6 perfluoroalkyl group, n represents 2 or 3, and M represents Li, Na, K or Ag, which comprises reacting a compound represented by the formula (V):

(HO)$_n$X (V)

wherein X and n are the same as the defined above, with a salt represented by the formula (VII):

(VII)

wherein $Y^1$, $Y^2$ and M are the same as defined above and Q represents a C1-C4 alkyl group.

<11> A process for production of a salt represented by the formula (I):

(I)

wherein X represents an n-valent connecting group, $Y^1$ and $Y^2$ each independently represent a fluorine atom or a C1-C6 perfluoroalkyl group, n represents 2 or 3, and $A^+$ represents an organic counter ion, which comprises reacting a salt represented by the formula (IV):

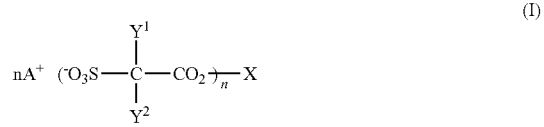
(IV)

wherein X, $Y^1$, $Y^2$ and n are the same as defined above, and M represents Li, Na, K or Ag, with a compound represented by the formula (VIII):

$A^+Z^-$ (VIII)

wherein $A^+$ is the same as defined above and Z represents F, Cl, Br, I, $BF_4$, $AsF_6$, $SbF_6$, $PF_6$ or $ClO_4$.

<12> A process for production of a salt represented by the formula (I):

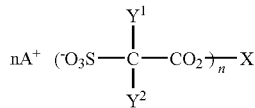
(I)

wherein X represents an n-valent connecting group, Y¹ and Y² each independently represent a fluorine atom or a C1-C6 perfluoroalkyl group, n represents 2 or 3, and A⁺ represents an organic counter ion, which comprises reacting a compound represented by the formula (V):

(V)

wherein X and n are the same as the defined above, with a salt represented by the formula (IX):

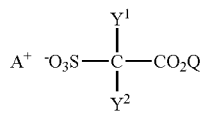
(IX)

wherein A⁺, Y¹ and Y² are the same as defined above and Q represents a C1-C4 alkyl group.

<13> A chemically amplified positive resist composition comprising a salt represented by the formula (I):

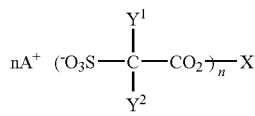
(I)

wherein X represents an n-valent connecting group, Y¹ and Y² each independently represent a fluorine atom or a C1-C6 perfluoroalkyl group, n represents 2 or 3, and A⁺ represents an organic counter ion, and a resin which contains a structural unit which has an acid-labile group and which itself is insoluble or poorly soluble in an aqueous alkali solution but becomes soluble in an aqueous alkali solution by the action of an acid.

<14>. The chemically amplified positive resist composition according to <13>, wherein Y¹ and Y² each independently represent a fluorine atom or a trifluoromethyl group.

<15> The chemically amplified positive resist composition according to <13> or <14>, wherein n is 2.

<16> The chemically amplified positive resist composition according to any one of <13> to <15>, wherein the organic counter ion is at least one cation selected from a cation represented by the formula (IIa):

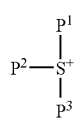
(IIa)

wherein P¹, P² and P³ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

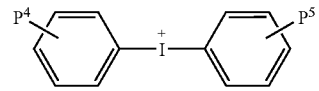
(IIb)

wherein P⁴ and P⁵ each independently represent a hydrogen atom, a hydroxyl group, a C1-C12 alkyl group or a C1-C12 alkoxy group, and a cation represented by the formula (IIc):

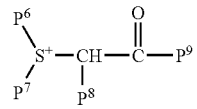
(IIc)

wherein P⁶ and P⁷ each independently represent a C1-C12 alkyl group or a C3-C12 cycloalkyl group, or P⁶ and P⁷ are bonded to form a C3-C12 divalent acyclic hydrocarbon group which forms a ring together with the adjacent S⁺, and at least one —CH₂— in the divalent acyclic hydrocarbon group may be replaced with —CO—, —O— or —S—, P⁸ represents a hydrogen atom, P⁹ represents a C1-C12 alkyl group, a C3-C12 cycloalkyl group or an aromatic group which may be substituted, or P⁸ and P⁹ are bonded to form a divalent acyclic hydrocarbon group which forms a 2-oxocycloalkyl group together with the adjacent —CHCO—, and at least one —CH₂— in the divalent acyclic hydrocarbon group may be replaced with —CO—, —O— or —S—.

<17> The chemically amplified positive resist composition according to any one of <13> to <15>, wherein the organic counter ion is a cation represented by the formula (IId):

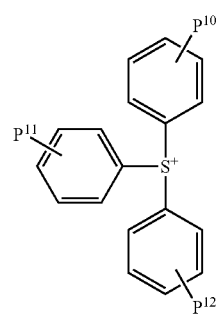
(IId)

wherein P¹⁰, P¹¹ and P¹² each independently represent a hydrogen atom or a C1-C4 alkyl group.

<18> The chemically amplified positive resist composition according to any one of <13> to <17>, wherein the n-valent connecting group is a C1-C30 n-valent hydrocarbon group which may be substituted with at least one selected from a C1-C6 alkoxy group, a C1-C4 perfluoroalkyl group, a C1-C6 hydroxyalkyl group, a hydroxyl group and a cyano group, and at least one —CH₂— in the C1-C30 n-valent hydrocarbon group may be replaced with —O— or —CO—.

<19> The chemically amplified positive resist composition according to <13>, wherein the salt of the formula (I) is a salt represented by the formula (IIIa), (IIIb) or (IIIc);

(IIIa)

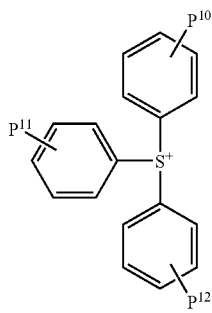

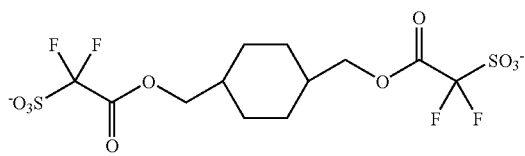

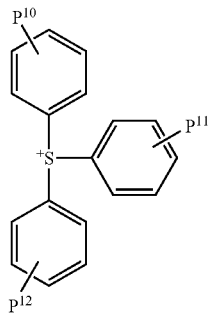

(IIIb)

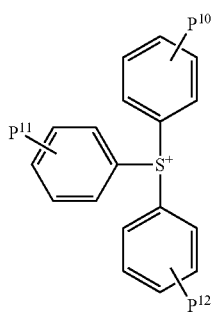

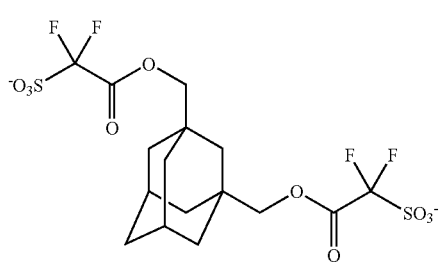

-continued

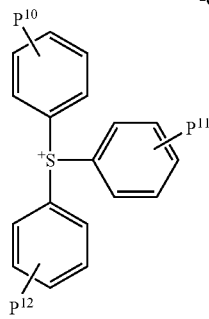

(IIIc)

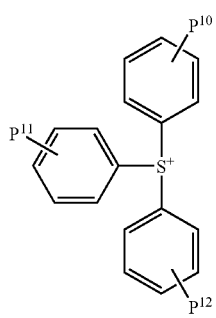

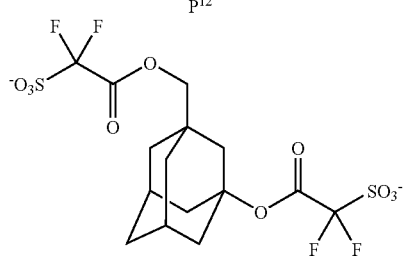

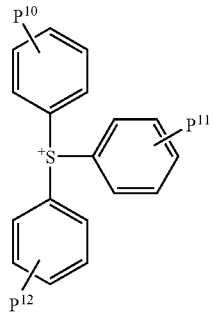

wherein $P^{10}$, $P^{11}$ and $P^{12}$ are the same as defined in claim 17.

<20> The chemically amplified positive resist composition according to any one of <13> to <19>, the resin contains a structural unit derived from a monomer having a bulky and acid-labile group.

<21> The chemically amplified positive resist composition according to <20>, the bulky and acid-labile group is a 2-alkyl-2-adamantyl ester group or a 1-(1-adamantyl)-1-alkylalkyl ester group.

<22> The chemically amplified positive resist composition according to <20>, the monomer having a bulky and acid-labile group is 2-alkyl-2-adamantyl acrylate, 2-alkyl-2-adamantyl methacrylate, 1-(1-adamantyl)-1-alkylalkyl acrylate, 1-(1-adamantyl)-1-alkylalkyl methacrylate, 2-alkyl-2-adamantyl 5-norbornene-2-carboxylate, 1-(1-adamantyl)-1- alkylalkyl 5-norbornene-2-carboxylate, 2-alkyl-2-adamantyl α-chloroacrylate or 1-(1-adamantyl)-1-alkylalkyl α-chloroacrylate.

<23> The chemically amplified positive resist composition according to <20>, the monomer having a bulky and acid-labile group is a 2-alkyl-2-adamantyl acrylate, a 2-alkyl-2-adamantyl methacrylate, a 2-alkyl-2-adamantyl α-chloroacrylate or a 1-(1-adamantyl)-1-alkylalkyl α-chloroacrylate.

<24> The chemically amplified positive resist composition according to <20>, the monomer having a bulky and acid-labile group is a 2-alkyl-2-adamantyl acrylate or a 2-alkyl-2-adamantyl methacrylate.

<25> The chemically amplified positive resist composition according to <20>, the monomer having a bulky and acid-labile group is 2-ethyl-2-adamantyl acrylate, 2-ethyl-2-adamantyl methacrylate, 2-isopropyl-2-adamantyl acrylate or 2-isopropyl-2-adamantyl methacrylate.

<26> The chemically amplified positive resist composition according to any one of <20> to <25>, the resin contains a structural unit derived from a monomer having an acid-stable group, in addition to the structural unit derived from a monomer having a bulky and acid-labile group.

<27> The chemically amplified positive resist composition according to <26>, the structural unit derived from the monomer having an acid-stable group is a structural unit derived from 3-hydroxy-1-adamantyl acrylate; a structural unit derived from 3-hydroxy-1-adamantyl methacrylate; a structural unit derived from 3,5-dihydroxy-1-adamantyl acrylate; a structural unit derived from 3,5-dihydroxy-1-adamantyl methacrylate; a structural unit derived from α-acryloyloxy-γ-butyrolactone; a structural unit derived from α-methacryloyloxy-γ-butyrolactone; a structural unit derived from β-acryloyloxy-γ-butyrolactone; a structural unit derived from β-methacryloyloxy-γ-butyrolactone; a structural unit represented by the formula (X):

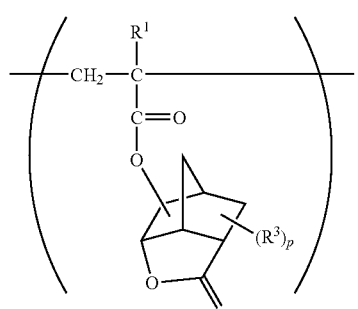

(X)

wherein $R^1$ represents a hydrogen atom or a methyl group, $R^3$ represents a methyl group, a trifluoromethyl group or a halogen atom, p represents an integer of 0 to 3, and when p represents 2 or 3, $R^3$s may be the same or different each other;

a structural unit represented by the formula (XI):

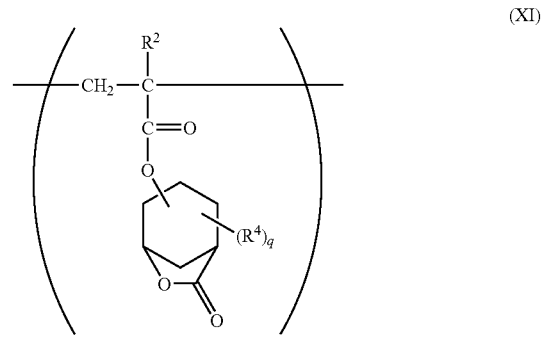

(XI)

wherein $R^2$ represents a hydrogen atom or a methyl group, $R^4$ represents a methyl group, a trifluoromethyl group or a halogen atom, q represents an integer of 0 to 3, and when q represents 2 or 3, $R^4$s may be the same or different each other;

a structural unit derived from p-hydroxystyrene;

a structural unit derived from m-hydroxystyrene;

a structural unit represented by the formula (XII):

(XII)

wherein $R^5$ and $R^6$ each independently represents a hydrogen atom, a C1-C3 alkyl group, a C1-C3 hydroxyalkyl group, a carboxyl group, a cyano group or a —COOU group in which U represents an alcohol residue, or $R^5$ and $R^6$ can be bonded together to form a carboxylic anhydride residue represented by —C(=O)OC(=O)—;

a structural unit represented by the formula (XIII):

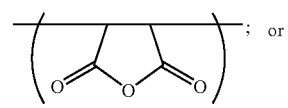

(XIII) ; or a structural unit represented by the formula (XIV):

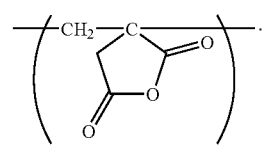

(XIV)

<28> The chemically amplified positive resist composition according to any one of <13> to <27>, wherein the chemically amplified positive resist composition further comprises a basic compound.

DESCRIPTION OF PREFERRED EMBODIMENTS

The present invention provides a salt represented by the formula (I):

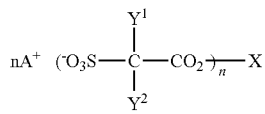
(I)

wherein X represents an n-valent connecting group, $Y^1$ and $Y^2$ each independently represent a fluorine atom or a C1-C6 perfluoroalkyl group, n represents 2 or 3, and $A^+$ represents an organic counter ion (hereinafter, simply referred to as Salt (I)).

Examples of the C1-C6 perfluoroalkyl group include a trifluoromethyl, pentafluoroethyl, heptafluoropropyl, nonafluorobutyl undecafluoropentyl and tridecafluorohexyl group, and the trifluoromethyl group is preferable.

$Y^1$ and $Y^2$ each independently preferably represent the fluorine atom or the trifluoromethyl group, and more preferably represents the fluorine atom. Preferably, n is 2.

Examples of the n-valent connecting group include an n-valent C1-C30 hydrocarbon group which may have at least one selected from a ring structure and a double bond, in which at least one —CH$_2$— may be replaced with —CO— or —O—, and in which at least one hydrogen atom may be replaced with at least one selected from a C1-C6 alkyl group, a C1-C6 alkoxy group, a C1-C4 perfluoroalkyl group, a C1-C6 hydroxyalkyl group, a hydroxyl group and a cyano group.

Examples of the C1-C6 alkyl group include a methyl, ethyl, n-propyl, isopropyl, n-butyl, sec-butyl, tert-butyl, n-pentyl and n-hexyl group. Examples of the C1-C6 alkoxy group include a methoxy, ethoxy, n-propoxy, isopropoxy, n-butoxy, sec-butoxy, tert-butoxy, n-pentyloxy and n-hexyloxy group. Examples of the C1-C4 perfluoroalkyl group include a trifluoromethyl, pentafluoroethyl, heptafluoropropyl and nonafluorobutyl group. Examples of the C1-C6 hydroxyalkyl group include a hydroxymethyl, 2-hydroxyethyl, 3-hydroxypropyl, 4-hydroxybutyl and 6-hydroxyhexyl group.

Examples of the ring structure include a cyclopentane, cyclohexane, decahydronaphthalene, norbornane, adamantane, benzene and naphthalene structure.

Specific examples of the n-valent connecting group include the followings:

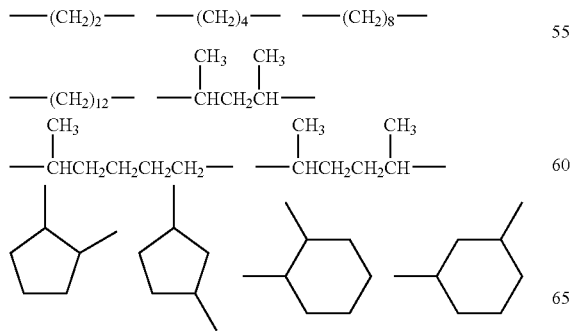

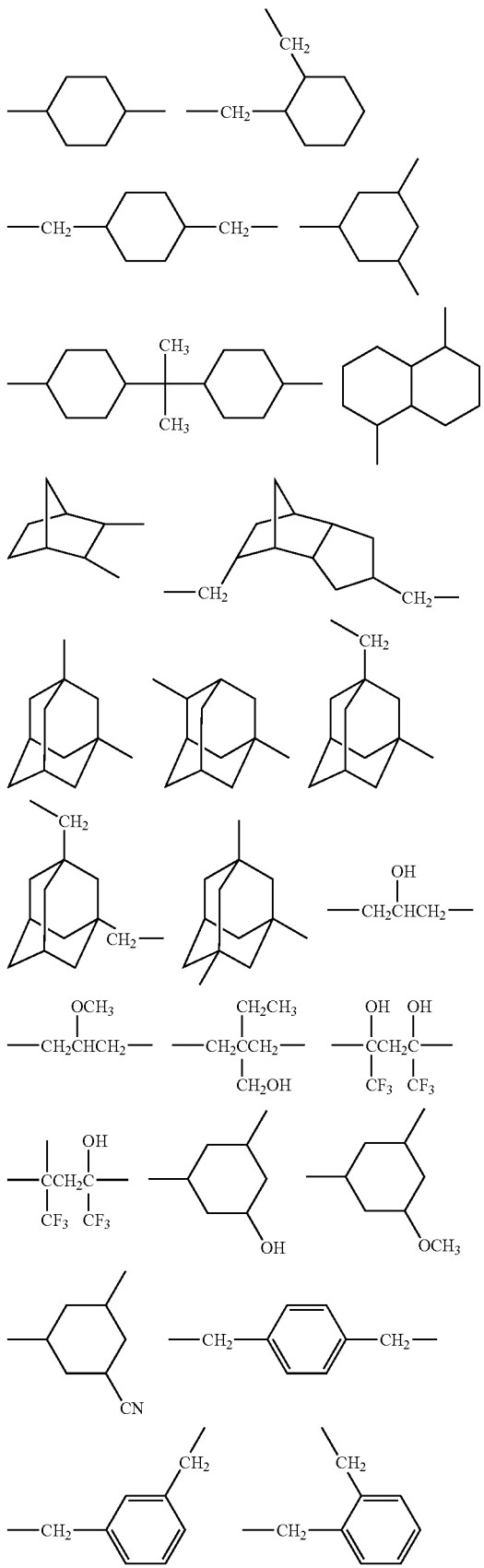

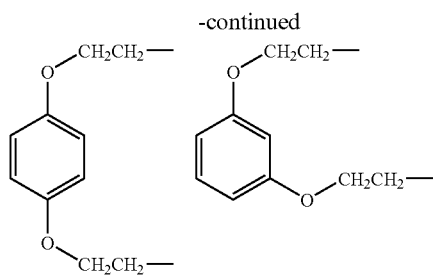
In the above formulae, the straight line with an open end shows a bond extended from an adjacent group.
Preferred n-valent connecting groups are followings:
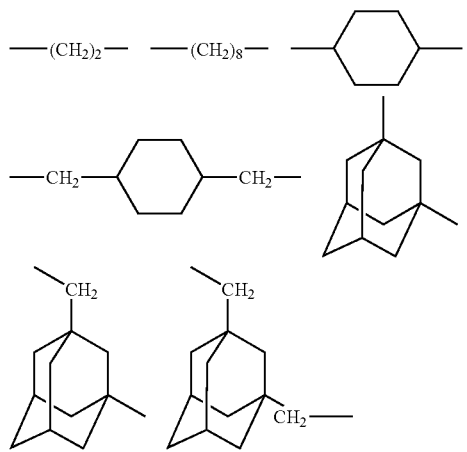
and more preferred are followings:
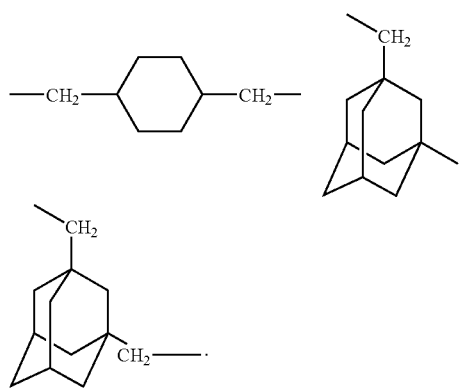
Specific examples of the anion part of Salt (I) include the followings:
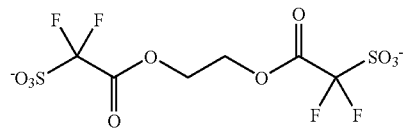
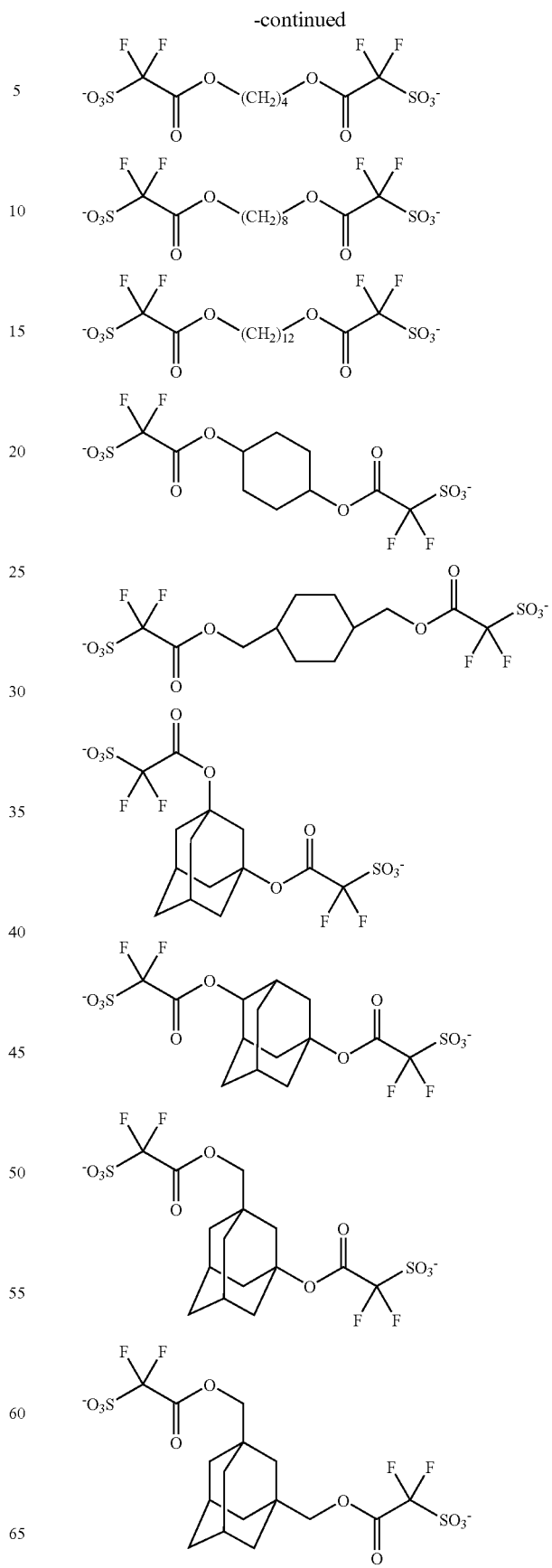

-continued
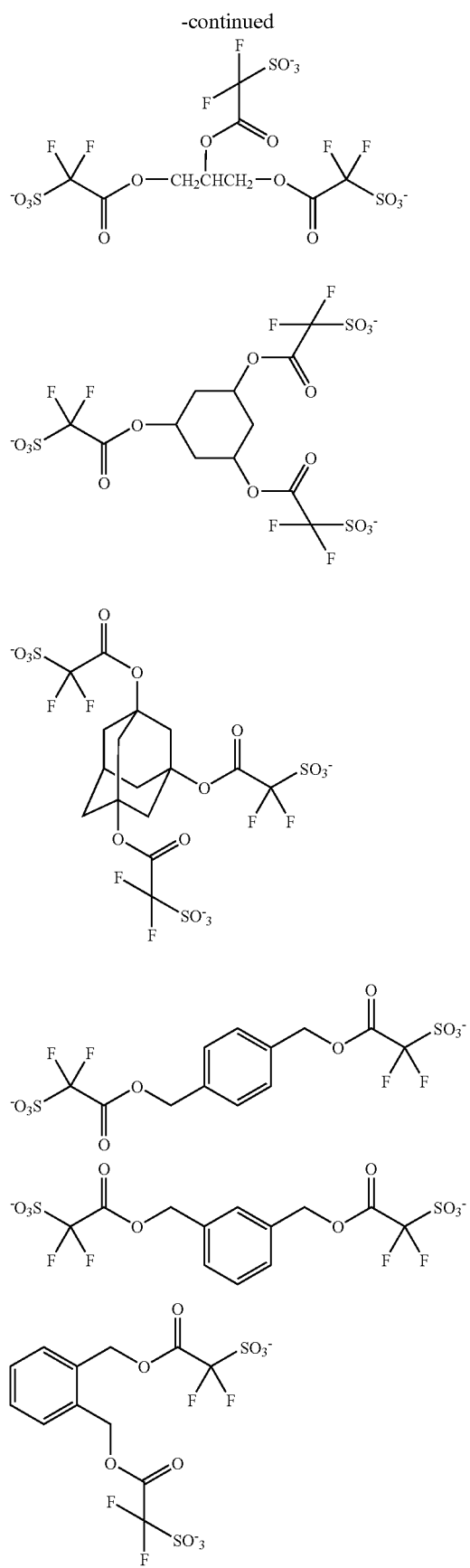
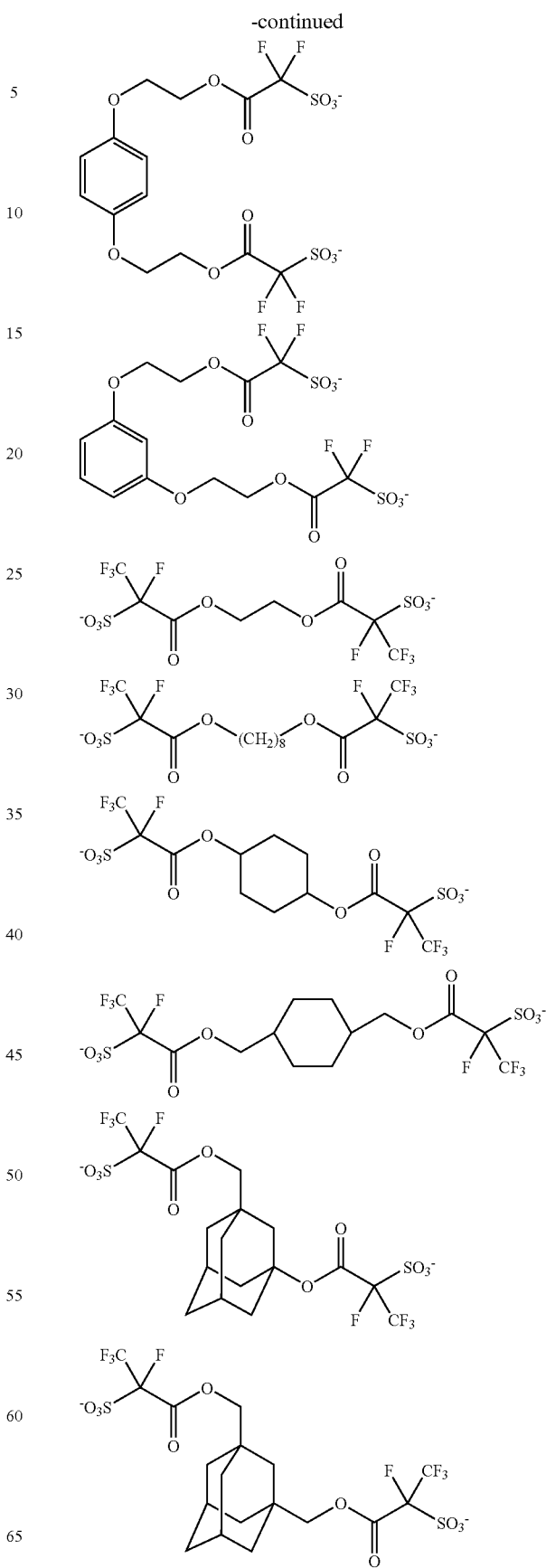

-continued

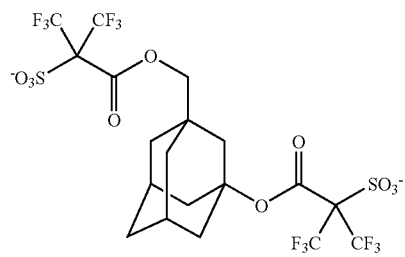

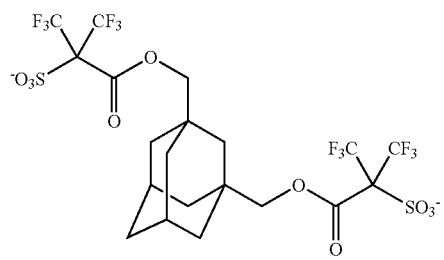

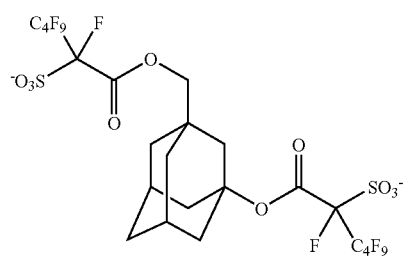

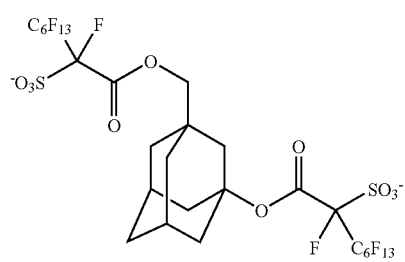

Among them, the following anion parts are preferable.

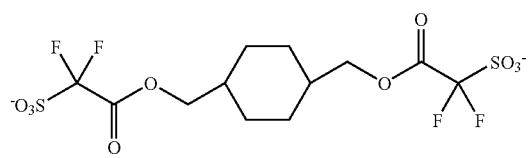

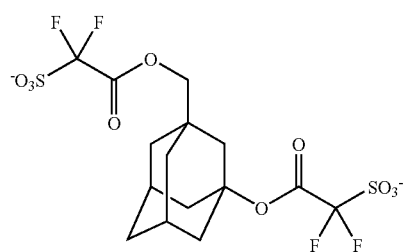

-continued

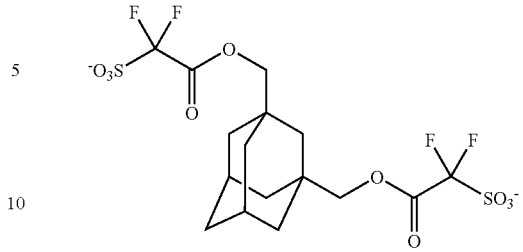

Examples of the organic counter ion include a cation represented by the formula (IIa):

(IIa)

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

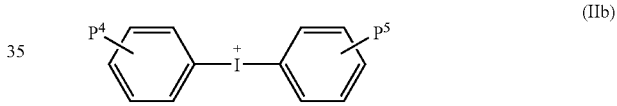
(IIb)

wherein $P^4$ and $P^5$ each independently represent a hydrogen atom, a hydroxyl group, a C1-C12 alkyl group or a C1-C12 alkoxy group, and a cation represented by the formula (IIc):

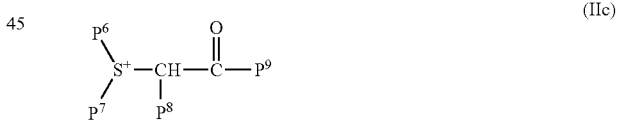
(IIc)

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —$CH_2$— in the divalent acyclic hydrocarbon group may be replaced with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ bond to form a divalent acyclic hydrocarbon group which forms a 2-oxocycloalkyl group together with the adjacent —CHCO—, and at least one —$CH_2$— in the divalent acyclic hydrocarbon group may be replaced with —CO—, —O— or —S—.

Examples of the C1-C12 alkoxy group in the formula (IIa) include a methoxy, ethoxy, n-propoxy, isopropoxy, n-butoxy, isobutoxy, sec-butoxy, tert-butoxy, n-pentyloxy, n-hexyloxy, n-octyloxy and 2-ethylhexyloxy group. Examples of the C3-C12 cyclic hydrocarbon group in the formula (IIa) include a cyclopentyl, cyclohexyl, 1-adamantyl, 2-adamantyl, phenyl, 2-methylphenyl, 4-methylphenyl, 1-naphthyl and 2-naphthyl group.

Examples of the C1-C30 alkyl group which may be substituted with at least one selected from the hydroxyl group, the C3-C12 cyclic hydrocarbon group and the C1-C12 alkoxy group in the formula (IIa) include a methyl, ethyl, n-propyl, isopropyl, n-butyl, isobutyl, sec-butyl, tert-butyl, n-pentyl, n-hexyl, n-octyl, 2-ethylhexyl and benzyl group.

Examples of the C3-C30 cyclic hydrocarbon group which may be substituted with at least one selected from the hydroxyl group and the C1-C12 alkoxy group in the formula (IIa) include a cyclopentyl, cyclohexyl, 1-adamantyl, 2-adamantyl, bicyclohexyl, phenyl, 2-methylphenyl, 4-methylphenyl, 4-ethylphenyl, 4-isopropylphenyl, 4-tert-butylphenyl, 2,4-dimethylphenyl, 2,4,6-trimethylphenyl, 4-n-hexylphenyl, 4-n-octylphenyl, 1-naphthyl, 2-naphthyl, fluorenyl, 4-phenylphenyl, 4-hydroxyphenyl, 4-methoxyphenyl, 4-tert-butoxyphenyl, 4-n-hexyloxyphenyl group.

Examples of the C1-C12 alkyl group in the formulae (IIb) and (IIc) include a methyl, ethyl, n-propyl, isopropyl, n-butyl, isobutyl, sec-butyl, tert-butyl, n-pentyl, n-hexyl, n-octyl and 2-ethylhexyl group. Examples of the C1-C12 alkoxy group in the formula (IIb) include the same groups as mentioned in the above formula (IIa).

Examples of the C3-C12 cycloalkyl group in the formula (IIc) include a cyclopropyl, cyclobutyl, cyclopentyl, cyclohexyl, cycloheptyl, cyclooctyl and cyclodecyl group. Examples of the C3-C12 divalent acyclic hydrocarbon group formed by bonding $P^6$ and $P^7$ include a trimethylene, tetramethylene, pentamethylene group. Examples of the ring group formed together with the adjacent $S^+$ and the divalent acyclic hydrocarbon group include a tetramethylenesulfonio, pentamethylenesulfonio and oxybisethylenesulfonio group.

Examples of the aromatic group in the formula (IIc) include a phenyl, tolyl, xylyl and naphthyl group. Examples of the divalent acyclic hydrocarbon group formed by bonding $P^8$ and $P^9$ include a methylene, ethylene, trimethylene, tetramethylene and pentamethylene group and examples of the 2-oxocycloalkyl group formed together with the adjacent —CHCO— and the divalent acyclic hydrocarbon group include a 2-oxocyclopentyl and 2-oxocyclohexyl group.

As the organic counter ion, a cation represented by the formula (IId):

$$\text{(IId)}$$

wherein $P^{10}$, $P^{11}$ and $P^{12}$ each independently represent a hydrogen atom or a C1-C4 alkyl group, is preferred.

Examples of the C1-C4 alkyl group in the formula (IId) include a methyl, ethyl, n-propyl, isopropyl, n-butyl, isobutyl, sec-butyl, tert-butyl group.

Examples of the cation represented by the formula (IIa) include the followings:

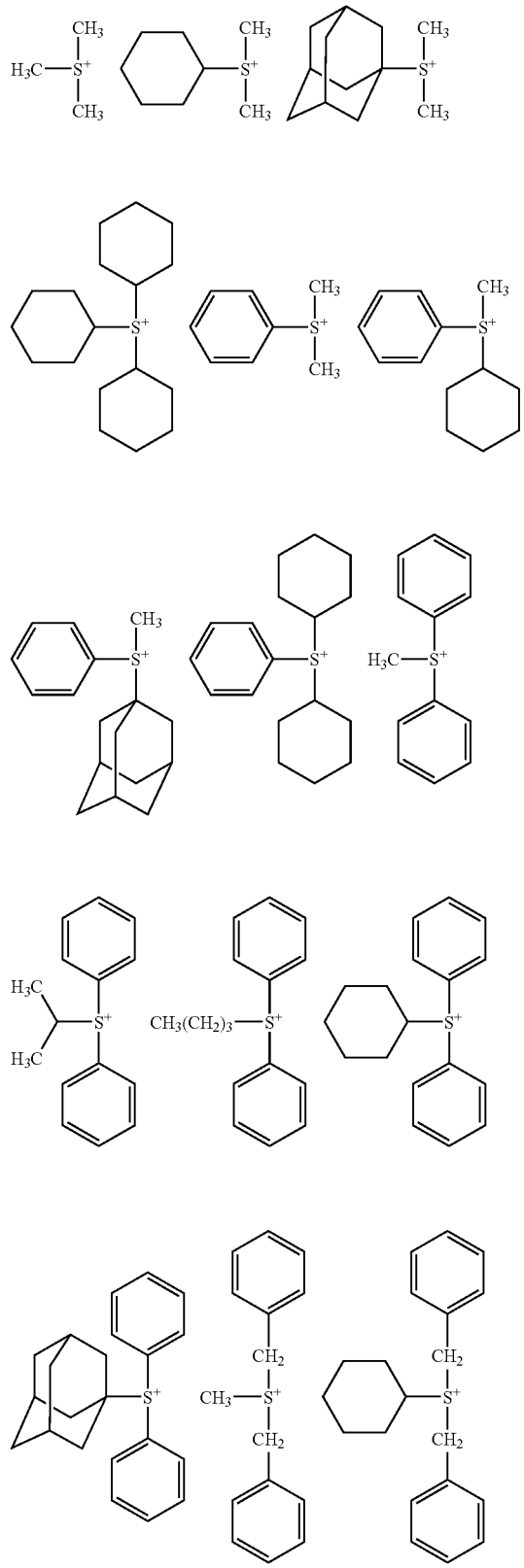

-continued
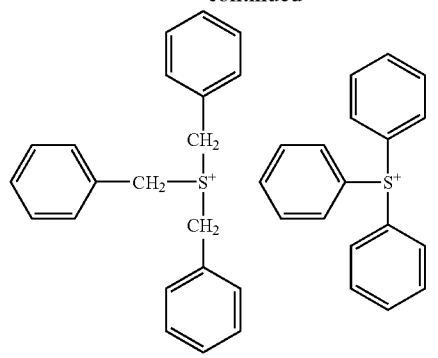
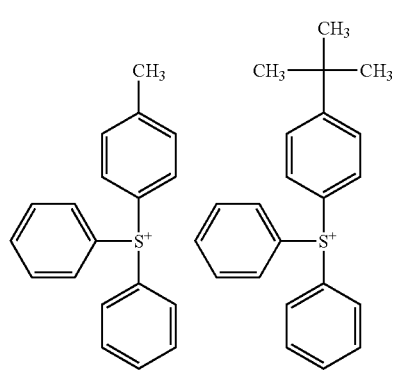
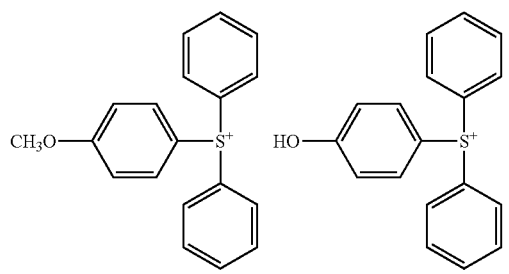
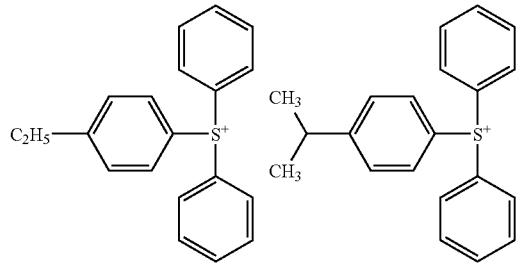
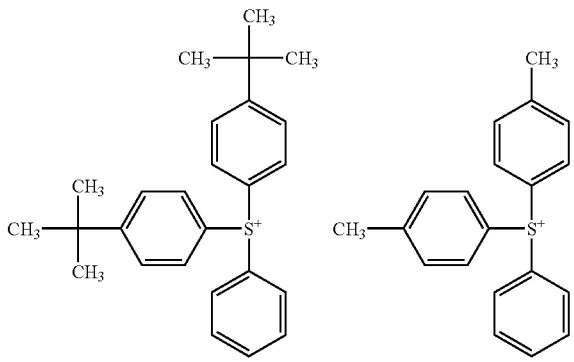
-continued
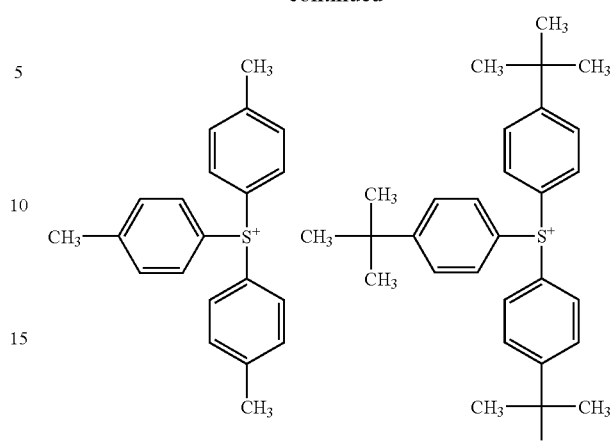
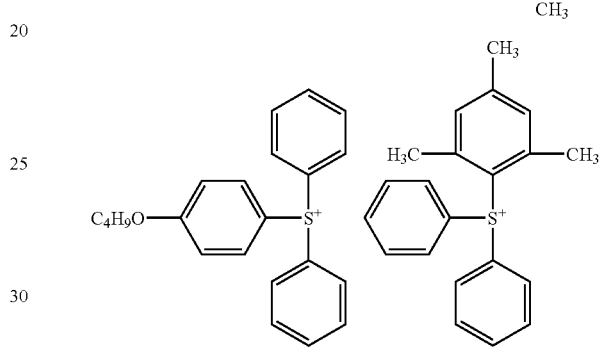
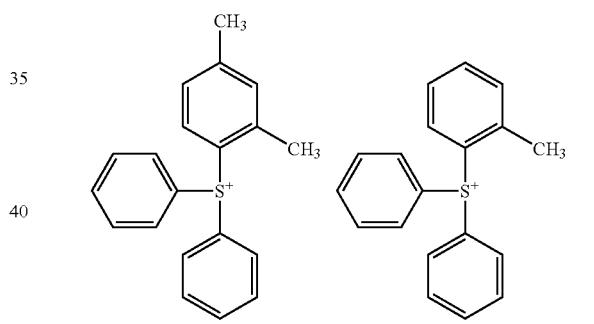
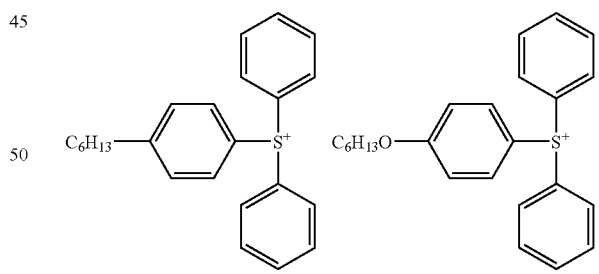
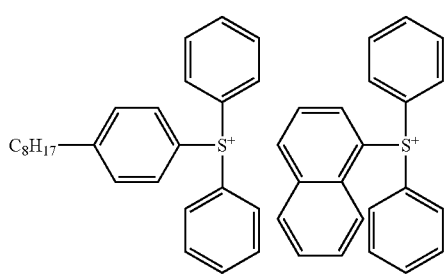

-continued
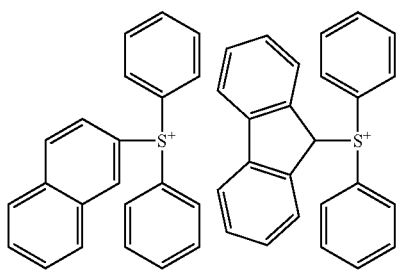
Examples of the cation represented by the formula (IIb) include the followings:
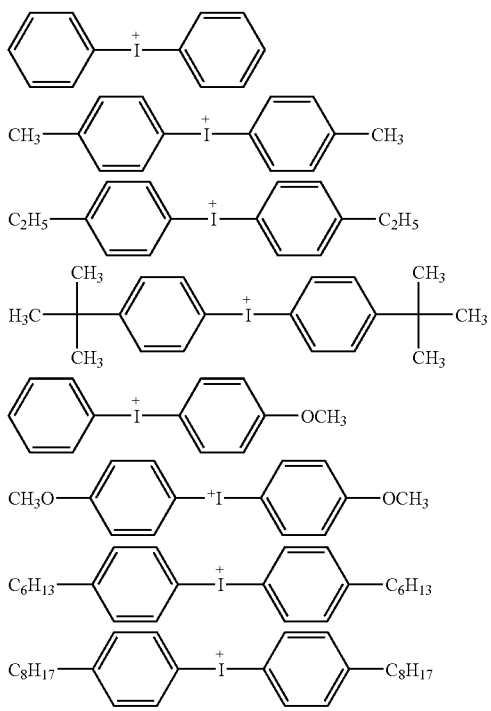
Examples of the cation represented by the formula (IIc) include followings:
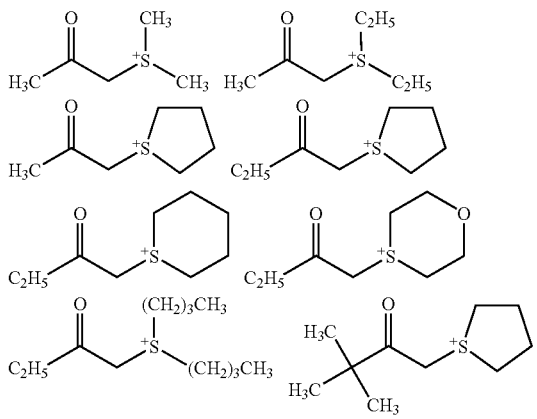
-continued
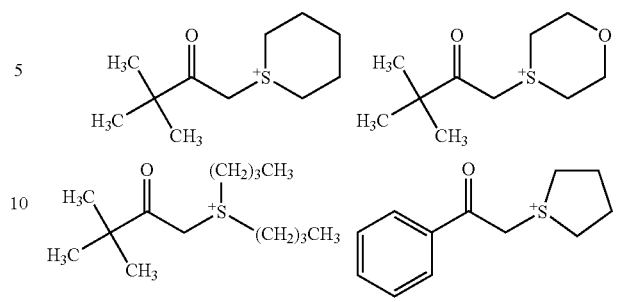
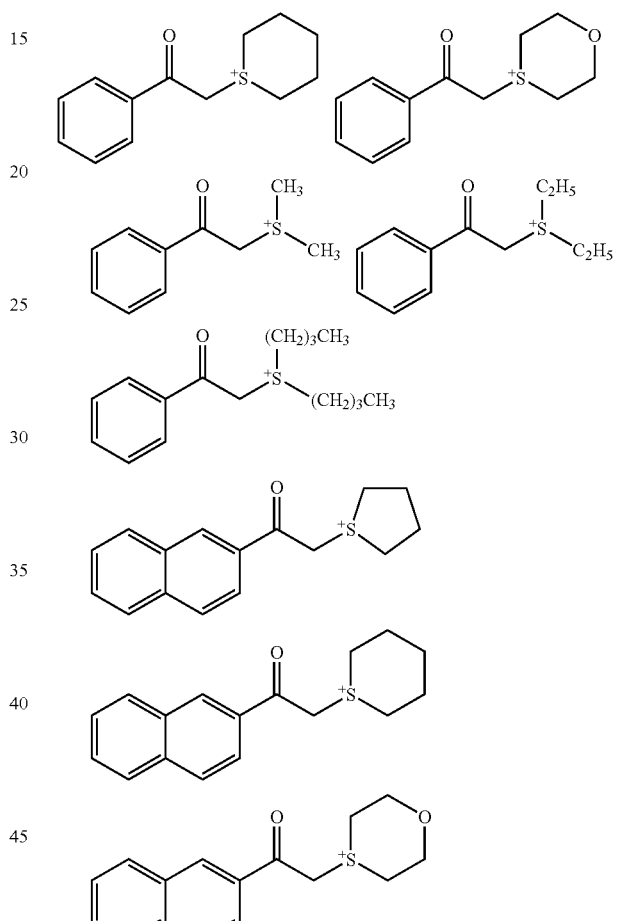
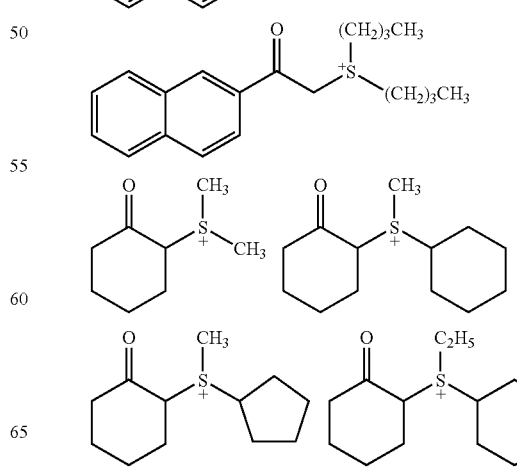

-continued
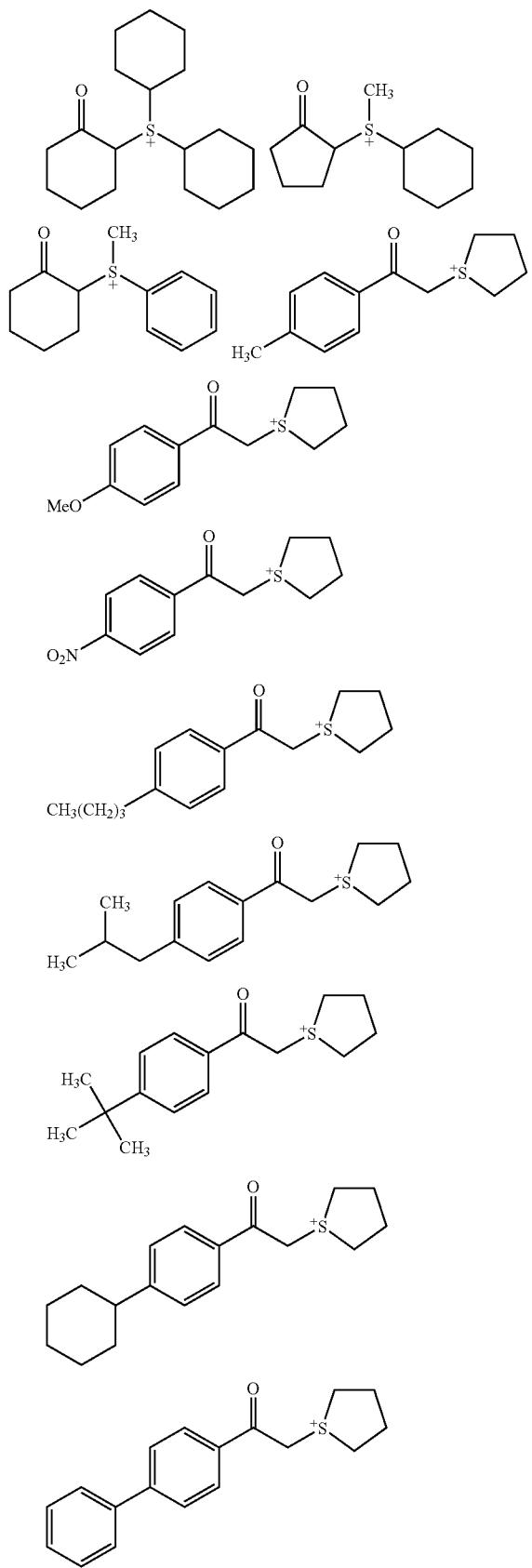
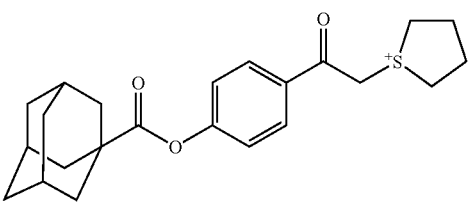
As Salt (I), the salt represented by the formula (IIIa):
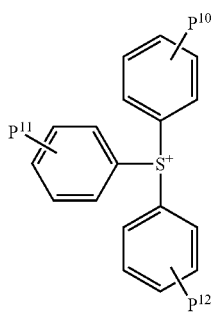
(IIIa)
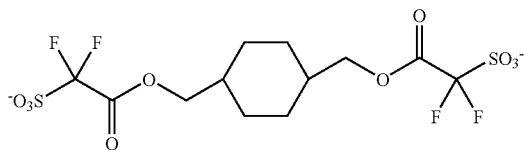
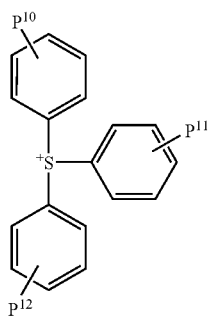
wherein $P^{10}$, $P^{11}$ and $P^{12}$ are the same as defined above, the salt represented by the formula (IIIb):
(IIIb)
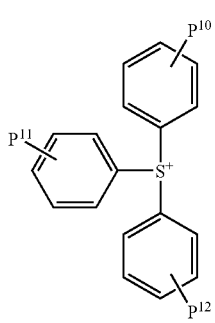

-continued

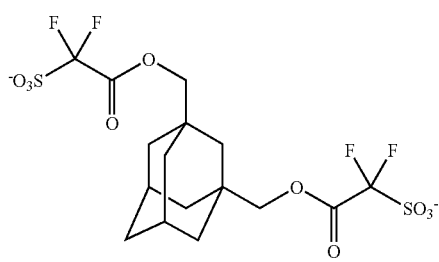

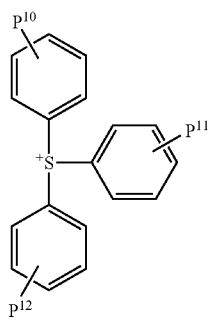

wherein $P^{10}$, $P^{11}$ and $P^{12}$ are the same as defined above, and the salt represented by the formula (IIIc):

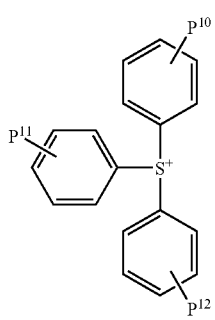                                                           (IIIc)

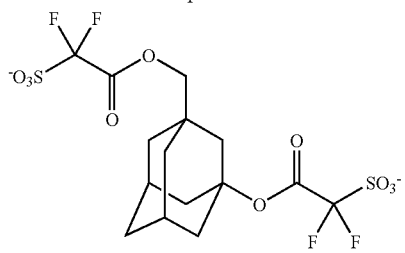

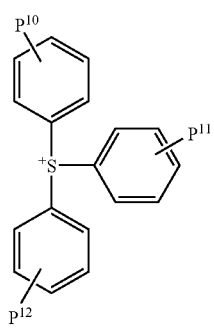

wherein $P^{10}$, $P^{11}$ and $P^{12}$ are the same as defined above, are preferred for providing chemically amplified resist compositions giving patterns having higher resolution and more excellent pattern shape.

Examples of the process for production of Salt (I) include a process comprising reacting a salt represented by the formula (IV):

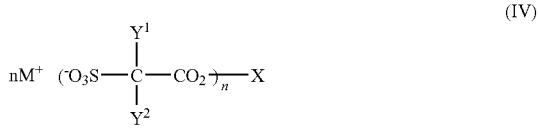                                                           (IV)

wherein X, $Y^1$, $Y^2$ and n are the same as defined above, and M represents Li, Na, K or Ag (hereinafter, simply referred to as the salt (IV)), with a compound represented by the formula (VIII):

$$A^+Z^- \quad \text{(VIII)}$$

wherein $A^+$ is the same as defined above and Z represents F, Cl, Br, I, $BF_4$, $AsF_6$, $SbF_6$, $PF_6$ or $ClO_4$ (hereinafter, simply referred to as the compound (VIII)), in an inert solvent such as acetonitrile, water, methanol, chloroform and dichloromethane, at a temperature of 0 to 150° C., preferably of 0 to 100° C.

As the compound (VIII), commercially available one is usually used.

The amount of the compound (VIII) to be used is usually 0.5 to 4 moles relative to 1 mole of the salt (IV). Salt (I) obtained may be taken out by crystallization or washing with water.

Salt (I) can be also produced by a process comprising reacting a compound of the formula (V):

                                                           (V)

wherein X and n are the same as the defined above (hereinafter, simply referred to as the compound (V)), with a salt of the formula (IX):

                                                           (IX)

wherein $A^+$, $Y^1$ and $Y^2$ are the same as defined above and Q represents a C1-C4 alkyl group (hereinafter, simply referred to as the salt (IX)).

As the compound (V), commercially available one is usually used.

Examples of the C1-C4 alkyl group include a methyl, ethyl, n-propyl, n-butyl and isobutyl group, and the methyl group is preferable.

The reaction of the compound (V) and the salt (IX) is usually conducted by mixing both in an aprotic solvent such as heptane, chloroform, dichloroethane, toluene, ethylbenzene, monochlorobenzene and acetonitrile, at 20 to 200° C., preferably 50 to 150° C. in the presence of an acid or base catalyst. Examples of the acid catalyst include an organic acid such as p-toluenesulfonic acid and an inorganic acid such as sulfuric acid. Examples of the base catalyst include a potassium alkoxide, lithium hydroxide, lithium amide and a titanium (IV) alkoxide.

The reaction is preferably conducted while removing the alcohol compound generated, for example, by Dean Stark method as the reaction time tends to be shortened.

The amount of the salt (IX) to be used is usually 2 to 5 moles, preferably 2 to 3 moles relative to 1 mole of the compound (V). The amount of the acid or base catalyst to be used is usually 0.001 to 5 moles, preferably 0.001 to 3 moles relative to 1 mole of the compound (V).

Examples of the process for production of the salt (IV) include a process comprising reacting the compound (V) with a salt represented by the formula (VI):

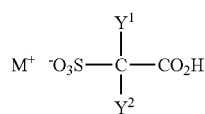

(VI)

wherein $Y^1$, $Y^2$ and M are the same as defined above (hereinafter, simply referred to as the salt (VI)).

The reaction of the compound (V) and the salt (VI) is usually conducted by mixing both in an aprotic solvent such as dichloroethane, toluene, ethylbenzene, monochlorobenzene, acetonitrile and N,N-dimethylformamide, at 20 to 200° C., preferably 50 to 150° C. in the presence of an acid catalyst or a dehydrating agent. Examples of the acid catalyst include an organic acid such as p-toluenesulfonic acid and an inorganic acid such as sulfuric acid. Examples of the dehydrating agent include 1,1'-carbonyldiimidazole and N,N'-dicyclohexylcarbodiimide.

In the case of using the acid catalyst, the reaction is preferably conducted with dehydration, for example, by Dean Stark method as the reaction time tends to be shortened.

The amount of the salt (VI) to be used is usually 0.2 to 5 moles, preferably 0.5 to 3 moles relative to 1 mole of the compound (V). The amount of the acid catalyst to be used may be catalytic amount or the amount equivalent to solvent, and is usually 0.001 to 5 moles relative to 1 mole of the compound (V). The amount of the dehydrating agent to be used is usually 0.2 to 5 moles, preferably 0.5 to 3 moles relative to 1 mole of the compound (V).

The salt (IV) can be also produced by a process comprising reacting the compound (V) with a salt represented by the formula (VII):

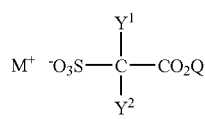

(VII)

wherein $Y^1$, $Y^2$ and M are the same as defined above and Q represents a C1-C4 alkyl group (hereinafter, simply referred to as the salt (VII)).

The reaction of the compound (V) and the salt (VII) is usually conducted by mixing both in the above-mentioned aprotic solvent, at 20 to 200° C., preferably 50 to 150° C. in the presence of the above-mentioned acid or base catalyst.

The above-mentioned reactions are preferably conducted while removing the alcohol compound generated, for example, by Dean Stark method as the reaction time tends to be shortened.

The amount of the salt (VII) is usually 2 to 5 moles, preferably 2 to 3 moles relative to 1 mole of the compound (V).

The amount of the acid or base catalyst to be used is usually 0.001 to 5 moles, preferably 0.001 to 3 moles relative to 1 mole of the compound (V).

Next, the present chemically amplified positive resist composition will be illustrated.

The present chemically amplified positive resist composition comprises Salt (I) and a resin containing a structural unit which has an acid-labile group and which itself is insoluble or poorly soluble in an aqueous alkali solution but becomes soluble in an aqueous alkali solution by the action of an acid.

Salt (I) is usually used as an acid generator, and the acid generated by irradiation to Salt (I) catalytically acts against acid-labile groups in the resin, cleaves acid-labile groups, and the resin becomes soluble in an alkali aqueous solution. Such a composition is suitable for chemically amplified positive resist composition.

The resin used for the present composition contains a structural unit which has the acid-labile group and which itself is insoluble or poorly soluble in an alkali aqueous solution, but the acid-labile group cleave by an acid.

In the present specification, "—COOR" may be described as "a structure having ester of carboxylic acid", and may also be abbreviated as "ester group". Specifically, "—COOC(CH$_3$)$_3$" may be described as "a structure having tert-butyl ester of carboxylic acid", or be abbreviated as "tert-butyl ester group".

Examples of the acid-labile group include a structure having ester of carboxylic acid such as alkyl ester group in which a carbon atom adjacent to the oxygen atom is quaternary carbon atom, alicyclic ester group in which a carbon atom adjacent to the oxygen atom is quaternary carbon atom, and a lactone ester group in which a carbon atom adjacent to the oxygen atom is quaternary carbon atom. The "quaternary carbon atom" means a "carbon atom joined to four substituents other than hydrogen atom".

Examples of the acid-labile group include an alkyl ester group in which a carbon atom adjacent to the oxygen atom is quaternary carbon atom such as a tert-butyl ester group; an acetal type ester group such as a methoxymethyl ester, ethoxymethyl ester, 1-ethoxyethyl ester, 1-isobutoxyethylester, 1-isopropoxyethylester, 1-ethoxypropoxyester, 1-(2-methoxyethoxy)ethyl ester, 1-(2-acetoxyethoxy)ethyl ester, 1-[2-(1-adamantyloxy)ethoxy]ethyl ester, 1-[2-(1-adamantanecarbonyloxy)ethoxy]ethyl ester, tetrahydro-2-furyl ester and tetrahydro-2-pyranyl ester group; an alicyclic ester group in which a carbon atom adjacent to the oxygen atom is quaternary carbon atom, such as an isobornyl ester, 1-alkylcycloalkyl ester, 2-alkyl-2-adamantyl ester and 1-(1-adamantyl)-1-alkylalkyl ester group. At least one hydrogen atom in the adamantyl group may be substituted with a hydroxyl group.

Examples of the structural unit include a structure unit derived from an ester of acrylic acid, a structural unit derived from an ester of methacrylic acid, a structural unit derived from an ester of norbornenecarboxylic acid, a structural unit derived from an ester of tricyclodecenecarboxylic acid and a structural unit derived from an ester of tetracyclodecenecarboxylic acid. The structure units derived from the ester of acrylic acid and from the ester of methacrylic acid are preferable.

The resin used for the present composition can be obtained by conducting polymerization reaction of a monomer or monomers having the acid-labile group and an olefinic double bond.

Among the monomers, those having a bulky and acid-labile group such as an alicyclic ester group (e.g. a 2-alkyl-2-adamantyl ester and 1-(1-adamantyl)-1-alkylalkyl ester group), since excellent resolution is obtained when the resin obtained is used in the present composition.

Examples of such monomer containing the bulky and acid-labile group include a 2-alkyl-2-adamantyl acrylate, a 2-alkyl-2-adamantyl methacrylate, 1-(1-adamantyl)-1-alkylalkyl acrylate, a 1-(1-adamantyl)-1-alkylalkyl methacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate.

Particularly when the 2-alkyl-2-adamantyl acrylate, the 2-alkyl-2-adamantyl methacrylate or the 2-alkyl-2-adamantyl α-chloroacrylate is used as the monomer for the resin component in the present composition, a resist composition having excellent resolution tend to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-methyl-2-adamantyl α-chloroacrylate and 2-ethyl-2-adamantyl α-chloroacrylate. When particularly 2-ethyl-2-adamantyl acrylate, 2-ethyl-2-adamantyl methacrylate, 2-isopropyl-2-adamantyl acrylate or 2-isopropyl-2-adamantyl methacrylate is used for the present composition, a resist composition having excellent sensitivity and heat resistance tends to be obtained. In the present invention, two or more kinds of monomers having a group or groups dissociated by the action of the acid may be used together, if necessary.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide.

The resin used for the present composition can also contain other structural unit or units derived from an acid-stable monomer in addition to the above-mentioned structural units having the acid-labile group. Herein, the "structural unit derived from an acid-stable monomer" means "a structural unit not dissociated by an acid generated from Salt (I)".

Examples of such other structural unit derived from the acid-stable monomer include a structural unit derived from a monomer having a free carboxyl group such as acrylic acid and methacrylic acid; a structural unit derived from an aliphatic unsaturated dicarboxylic anhydride such as maleic anhydride and itaconic anhydride; a structural unit derived from 2-norbornene; a structural unit derived from acrylonitrile or methacrylonitrile; a structural unit derived from an alkyl acrylate or an alkyl methacrylate in which a carbon atom adjacent to oxygen atom is secondary or tertiary carbon atom; a structural unit derived from 1-adamantyl acrylate or 1-adamantyl methacrylate; a structural unit derived from styrene monomer such as p-hydroxystyrene and m-hydroxystyrene; a structural unit derived from acryloyloxy-γ-butyrolactone or methacryloyloxy-γ-butyrolactone having a lactone ring which may be substituted with an alkyl group; and the like. Herein, the 1-adamantyloxycarbonyl group is the acid-stable group though the carbon atom adjacent to oxygen atom is the quaternary carbon atom, and the 1-adamantyloxycarbonyl group may be substituted with at least one hydroxyl group.

Specific examples of the structural unit derived from the acid-stable monomer include a structural unit derived from 3-hydroxy-1-adamantyl acrylate;

a structural unit derived from 3-hydroxy-1-adamantyl methacrylate;

a structural unit derived from 3,5-dihydroxy-1-adamantyl acrylate;

a structural unit derived from 3,5-dihydroxy-1-adamantyl methacrylate;

a structural unit derived from α-acryloyloxy-γ-butyrolactone;

a structural unit derived from α-methacryloyloxy-γ-butyrolactone;

a structural unit derived from β-acryloyloxy-γ-butyrolactone;

a structural unit derived from β-methacryloyloxy-γ-butyrolactone;

a structural unit represented by the formula (X):

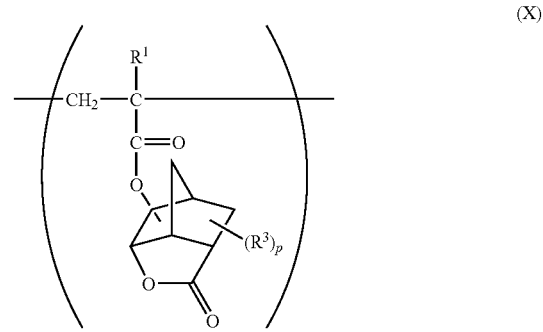

wherein $R^1$ represents a hydrogen atom or a methyl group, $R^3$ represents a methyl group, a trifluoromethyl group or a halogen atom, p represents an integer of 0 to 3, and when p represents 2 or 3, $R^3$s may be the same or different each other;

a structural unit represented by the formula (XI):

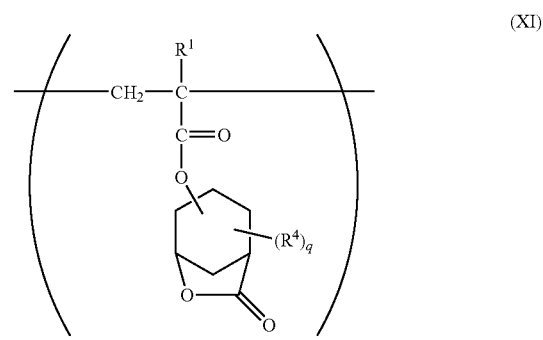

wherein $R^2$ represents a hydrogen atom or a methyl group, $R^4$ represents a methyl group, a trifluoromethyl group or a halogen atom, q represents an integer of 0 to 3, and when q represents 2 or 3, $R^4$s may be the same or different each other;

a structural unit derived from p-hydroxystyrene;

a structural unit derived from m-hydroxystyrene;

a structural unit derived from an alicyclic compound having an olefinic double bond such as a structural unit represented by the formula (XII):

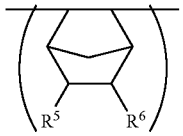

(XII)

wherein $R^5$ and $R^6$ each independently represents a hydrogen atom, a C1-C3 alkyl group, a C1-C3 hydroxyalkyl group, a carboxyl group, a cyano group or a —COOU group in which U represents an alcohol residue, or $R^5$ and $R^6$ can be bonded together to form a carboxylic anhydride residue represented by —C(=O)OC(=O)—;

a structural unit derived from an aliphatic unsaturated dicarboxylic anhydride such as a structural unit represented by the formula (XIII):

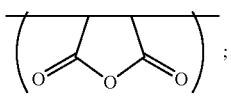

(XIII)

a structural unit represented by the formula (XIV):

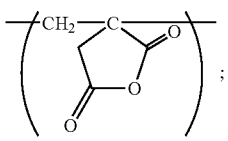

(XIV)

and the like.

Particularly, the resin having further at least one structural unit selected from the structural unit derived from p-hydroxystyrene, the structural unit derived from m-hydroxystyrene, the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantyl methacrylate, the structural unit represented by the formula (X) and the structural unit represented by the formula (XI) in addition to the structural unit having the acid-labile group is preferable from the standpoint of the adhesiveness of resist to a substrate and resolution of resist.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting corresponding hydroxyadamantane with acrylic acid, methacrylic acid or its acid halide, and they are also commercially available.

Further, the acryloyloxy-γ-butyrolactone and the methacryloyloxy-γ-butyrolactone having the lactone ring which may be substituted with the alkyl group can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

As monomers to give structural units represented by the formulae (X) and (XI), specifically listed are, for example, an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446 A.

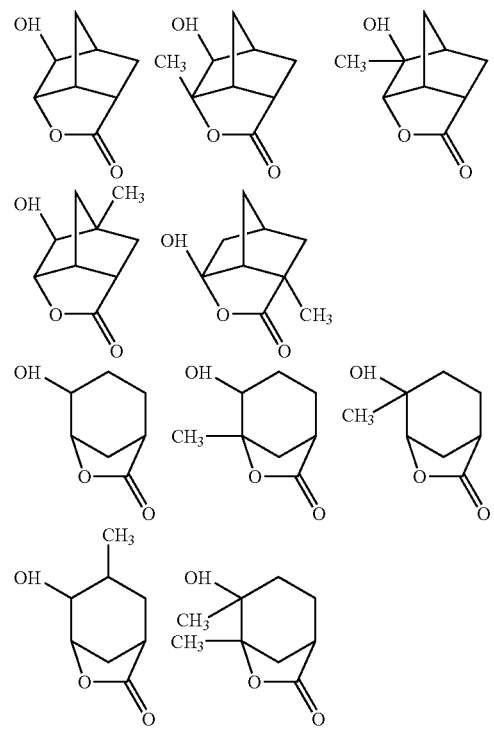

Examples of the acryloyloxy-γ-butyrolactone and the methacryloyloxy-γ-butyrolactone having the lactone ring which may be substituted with the alkyl group include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone and β-methacryloyloxy-α-methyl-γ-butyrolactone.

In the case of KrF lithography, even in the case of using a structure unit derived from hydroxystyrene such as p-hydroxystyrene and m-hydroxystyrene, as one of components of the resin, a resist composition having sufficient transparency can be obtained. For obtaining such copolymerization resins, the corresponding acrylic or methacrylic ester monomer can be radical-polymerized with acetoxystyrene and styrene, and then the acetoxy group in the structure unit derived from acetoxystyrene can be de-acetylated with an acid.

The resin containing a structural unit derived from 2-norbornene shows strong structure because the alicyclic group is directly present on its main chain and shows a property that dry etching resistance is excellent. The structural unit derived from 2-norbornene can be introduced into the main chain by radical polymerization using, for example, an aliphatic unsaturated dicarboxylic anhydride such as maleic anhydride and itaconic anhydride together in addition to corresponding 2-norbornene. The structural unit derived from 2-norbornene is formed by opening of its double bond, and can be represented by the above-mentioned formula (XII). The structural unit derived from maleic anhydride and from itaconic anhydride which are the structural unit derived from aliphatic unsaturated dicarboxylic anhydrides are formed by opening of their double bonds, and can be represented by the above-mentioned formula (XIII) and the formula (XIV), respectively.

In $R^5$ and $R^6$, examples of the C1-C3 alkyl group include a methyl, ethyl, and n-propyl group, and examples of the C1-C3 hydroxyalkyl group include a hydroxymethyl and 2-hydroxyethyl group.

In $R^5$ and $R^6$, the —COOU group is an ester formed from the carboxyl group, and as the alcohol residue corresponding to U, for example, an optionally substituted C1-C8 alkyl group, 2-oxooxolan-3-yl group, 2-oxooxolan-4-yl and the like are listed, and as the substituent on the C1-C8 alkyl group, a hydroxyl group, an alicyclic hydrocarbon residue and the like are listed.

Specific examples of the monomer used to give the structural unit represented by the above-mentioned formula (XII) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (XII) is a structural unit having the acid-labile group even if it has the norbornene structure. Examples of monomers giving structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate, 1-(1-adamantyl)-1-methylethyl 5-norbornene-2-carboxylate, and the like.

The resin used in the present composition preferably contains the structural unit or units having the acid-labile group generally in a ratio of 10 to 80% by mole in all structural units of the resin though the ratio varies depending on the kind of radiation for patterning exposure, the kind of the acid-labile group, and the like.

When the structural units particularly derived from the 2-alkyl-2-adamantyl acrylate, the 2-alkyl-2-adamantyl methacrylate, the 1-(1-adamantyl)-1-alkylalkyl acrylate or the 1-(1-adamantyl)-1-alkylalkyl methacrylate are used as the structural unit having the acid-labile group, it is advantageous in dry-etching resistance of the resist that the ratio of the structural units is 15% by mole or more in all structural units of the resin.

When, in addition to structural units having the acid-labile group, other structural units having the acid-stable group are contained in the resin, it is preferable that the sum of these structural units is in the range of 20 to 90% by mole based on all structural units of the resin.

The resin used for the present composition can be produced by conducting polymerization reaction of the corresponding monomer or monomers. The resin can be also produced by conducting oligomerization of the corresponding monomer or monomers followed by polymerizing the oligomer obtained.

The polymerization reaction is usually carried out in the presence of a radical initiator.

The radical initiator is not limited and examples thereof include an azo compound such as 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile), 2,2'-azobis(2,4-dimethyl-4-methoxyvaleronitrile), dimethyl-2,2'-azobis(2-methylpropionate) and 2,2'-azobis(2-hydroxymethylpropionitrile); an organic hydroperoxide such as lauroyl peroxide, tert-butyl hydroperoxide, benzoyl peroxide, tert-butyl peroxybenzoate, cumene hydroperoxide, diisopropyl peroxydicarbonate, di-n-propyl peroxydicarbonate, tert-butyl peroxyneodecanoate, tert-butyl peroxypivalate and 3,5,5-trimethylhexanoyl peroxide; and an inorganic peroxide such as potassium peroxodisulfate, ammonium peroxodisulfate and hydrogen peroxide. Among them, the azo compound is preferable and 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile) and dimethyl-2,2'-azobis(2-methylpropionate) are more preferable, and 2,2'-azobisisobutyronitrile and 2,2'-azobis(2,4-dimethylvaleronitrile) are especially preferable.

These radical initiators may be used alone or in a form of a mixture of two or more kinds thereof. When the mixture of two or more kinds thereof is used, the mixed ratio is not particularly limited.

The amount of the radical initiator is preferably 1 to 20% by mole based on all monomer or oligomer molar amount.

The polymerization temperature is usually 0 to 150° C., and preferably 40 to 100° C.

The polymerization reaction is usually carried out in the presence of a solvent and it is preferred to use a solvent which is sufficient to dissolve the monomer, the radical initiator and the resin obtained. Examples thereof include a hydrocarbon solvent such as toluene; an ether solvent such as 1,4-dioxane and tetrahydrofuran; a ketone solvent such as methyl isobutyl ketone; an alcohol solvent such as isopropyl alcohol; a cyclic ester solvent such as γ-butyrolactone; a glycol ether ester ester solvent such as propylene glycol monomethyl ether acetate; and an acyclic ester solvent such as ethyl lactate. These solvents may be used alone and a mixture thereof may be used.

The amount of the solvent is not limited, and practically, it is preferably 1 to 5 parts by weight relative to 1 part of all monomers or oligomers.

When an alicyclic compound having an olefinic double bond and an aliphatic unsaturated dicarboxylic anhydride are used as monomers, it is preferable to use them in excess amount in view of a tendency that these are not easily polymerized.

After competition of the polymerization reaction, the resin produced can be isolated, for example, by adding a solvent in which the present resin is insoluble or poorly soluble to the reaction mixture obtained and filtering the precipitated resin. If necessary, the isolated resin may be purified, for example, by washing with a suitable solvent.

The present resist composition preferably includes 80 to 99.9% by weight of the resin component and 0.1 to 20% by weight of Salt (I) based on the total amount of the resin component and Salt (I).

In the present resist composition, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

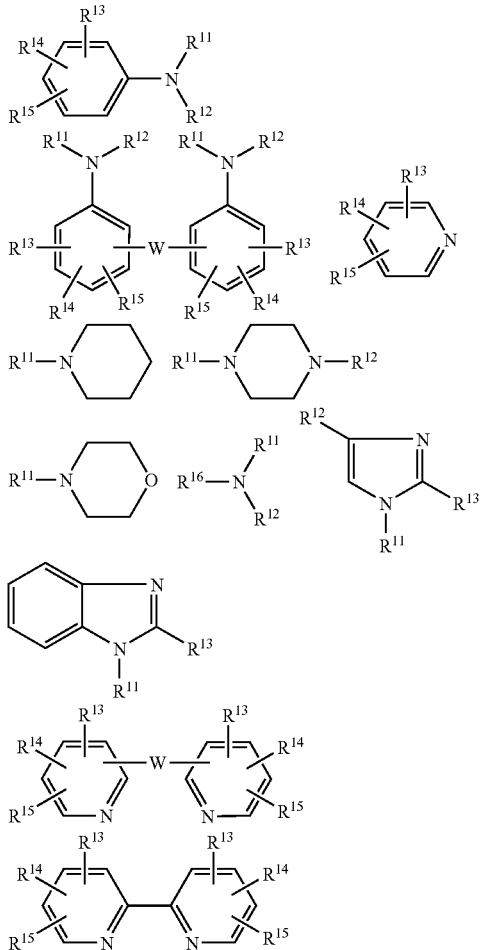

wherein $R^{11}$ and $R^{12}$ independently represent a hydrogen atom, an alkyl group, a cycloalkyl group or an aryl group, and the alkyl, cycloalkyl and aryl group may be substituted with at least one group selected from a hydroxyl group, an amino group which may be substituted with a C1-C4 alkyl group and a C1-C6 alkoxy group which may be substituted with a C1-C6 alkoxy group, $R^{13}$ and $R^{14}$ independently represent a hydrogen atom, an alkyl group, a cycloalkyl group, an aryl group or an alkoxy group, and the alkyl, cycloalkyl, aryl and alkoxy group may be substituted with at least one group selected from a hydroxyl group, an amino group which may be substituted with a C1-C4 alkyl group and a C1-C6 alkoxy group, or $R^{13}$ and $R^{14}$ bond together with the carbon atoms to which they bond to form an aromatic ring, $R^{15}$ represent a hydrogen atom, an alkyl group, a cycloalkyl group, an aryl group, an alkoxy group or a nitro group, and the alkyl, cycloalkyl, aryl and alkoxy group which may be substituted with at least one group selected from a hydroxyl group, an amino group which may be substituted with a C1-C4 alkyl group and a C1-C6 alkoxy group, $R^{16}$ represents an alkyl or cycloalkyl group, and the alkyl and cycloalkyl group may be substituted with at least one group selected from a hydroxyl group, an amino group which may be substituted with a C1-C4 alkyl group and a C1-C6 alkoxy group, and W represents —CO—, —NH—, —S—, —S—S—, an alkylene group of which at least one methylene group may be replaced with —O—, or an alkenylene group of which at least one methylene group may be replaced with —O—, and a quaternary ammonium hydroxide represented by the following formula:

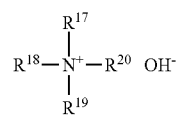

wherein $R^{17}$, $R^{18}$, $R^{19}$ and $R^{20}$ independently represent an alkyl group, a cycloalkyl group or an aryl group, and the alkyl, cycloalkyl and aryl group may be substituted with at least one group selected from a hydroxyl group, an amino group which may be substituted with a C1-C4 alkyl group and a C1-C6 alkoxy group.

The alkyl group in $R^{11}$, $R^{12}$, $R^{13}$, $R^{14}$, $R^{15}$, $R^{16}$, $R^{17}$, $R^{18}$, $R^{19}$ and $R^{20}$ preferably has about 1 to 10 carbon atoms, and more preferably has about 1 to 6 carbon atoms.

Examples of the amino group which may be substituted with the C1-C4 alkyl group include an amino, methylamino, ethylamino, n-butylamino, dimethylamino and diethylamino group. Examples of the C1-C6 alkoxy group which may be substituted with the C1-C6 alkoxy group include a methoxy, ethoxy, n-propoxy, isopropoxy, n-butoxy, tert-butoxy, n-pentyloxy, n-hexyloxy and 2-methoxyethoxy group.

Specific examples of the alkyl group which may be substituted with at least one group selected from a hydroxyl group, an amino group which may be substituted with a C1-C4 alkyl group, and a C1-C6 alkoxy group which may be substituted with a C1-C6 alkoxy group include a methyl, ethyl, n-propyl, isopropyl, n-butyl, tert-butyl, n-pentyl, n-hexyl, n-octyl, n-nonyl, n-decyl, 2-(2-methoxyethoxy)ethyl, 2-hydroxyethyl, 2-hydroxypropyl, 2-aminoethyl, 4-aminobutyl and 6-aminohexyl group.

The cycloalkyl group in $R^{11}$, $R^{12}$, $R^{13}$, $R^{14}$, $R^{15}$, $R^{16}$, $R^{17}$, $R^{18}$, $R^{19}$ and $R^{20}$ preferably has about 5 to 10 carbon atoms. Specific examples of the cycloalkyl group which may be substituted with at least one group selected from a hydroxyl group, an amino group which may be substituted with a C1-C4 alkyl group and a C1-C6 alkoxy group include a cyclopentyl, cyclohexyl, cycloheptyl and cyclooctyl group.

The aryl group in $R^{11}$, $R^{12}$, $R^{13}$, $R^{14}$, $R^{15}$, $R^{17}$, $R^{18}$, $R^{19}$ and $R^{20}$ preferably has about 6 to 10 carbon atoms. Specific examples of the aryl group which may be substituted with at least one group selected from a hydroxyl group, an amino group which may be substituted with a C1-C4 alkyl group and a C1-C6 alkoxy group include a phenyl and naphthyl group.

The alkoxy group in $R^{13}$, $R^{14}$ and $R^{15}$ preferably has about 1 to 6 carbon atoms and specific examples thereof include a methoxy, ethoxy, n-propoxy, isopropoxy, n-butoxy, tert-butoxy, n-pentyloxy and n-hexyloxy group.

The alkylene and alkenylene groups in W preferably have 2 to 6 carbon atoms. Specific examples of the alkylene group include an ethylene, trimethylene, tetramethylene, methylenedioxy and ethylene-1,2-dioxy group, and specific examples of the alkenylene group include an ethane-1,2-diyl, 1-propene-1,3-diyl and 2-butene-1,4-diyl group.

Specific examples of the amine compound include n-hexylamine, n-heptylamine, n-octylamine, n-nonylamine, n-decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptyamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecyamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skelton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.01 to 1% by weight of the basic compound based on the total amount of the resin component and Salt (I).

The present resist composition can contain, if necessary, a small amount of various additives such as a sensitizer, a solution suppressing agent, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A resist film applied onto the substrate and then dried is subjected to exposure for patterning, then heat-treated to facilitate a deblocking reaction, and thereafter developed with an alkali developer. The alkali developer used may be any one of various alkaline aqueous solution used in the art. Generally, an aqueous solution of tetramethylammonium hydroxide or (2-hydroxyethyl)trimethylammonium hydroxide (commonly known as "choline") is often used.

It should be construed that embodiments disclosed here are examples in all aspects and not restrictive. It is intended that the scope of the present invention is determined not by the above descriptions but by appended Claims, and includes all variations of the equivalent meanings and ranges to the Claims.

The present invention will be described more specifically by Examples, which are not construed to limit the scope of the present invention. The "%" and "part(s)" used to represent the content of any component and the amount of any material to be used in the following Examples are on a weight basis unless otherwise specifically noted. The weight-average molecular weight of any material in the following Examples is a value found by gel permeation chromatography [HLC-8120GPC Type, Column (Total 3 Columns): TSKgel Multipore HXL-M manufactured by TOSOH CORPORATION, Solvent: tetrahydrofuran] using polystyrene as a standard reference material.

Structures of salts obtained were determined by NMR (GX-270 Type or EX-270 Type, manufactured by JEOL LTD.) and mass spectrometry (Liquid Chromatography: 1100 Type manufactured by AGILENT TECHNOLOGIES LTD., Mass Spectrometry: LC/MSD Type or LC/MSD TOF Type manufactured by AGILENT TECHNOLOGIES LTD.).

Salt Synthesis Example 1

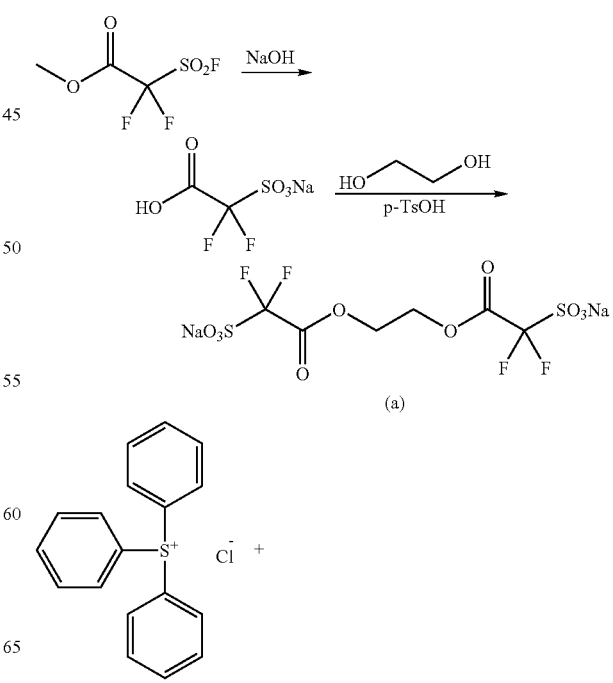

-continued

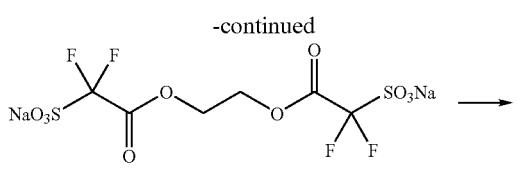

(a)

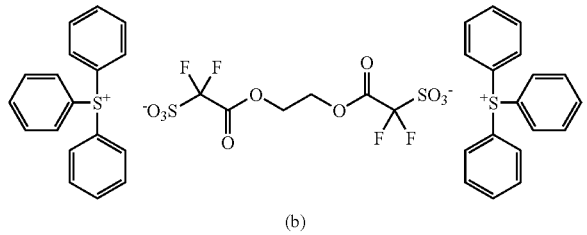

(b)

(1) 1140 Parts of 30% aqueous sodium hydroxide solution was added dropwise into a mixture of 500 parts of methyl difluoro(fluorosulfonyl)acetate and 750 parts of ion-exchanged water in an ice bath. The resultant mixture was stirred at room temperature for 15 hours and then neutralized with 390 parts of conc. hydrochloric acid. 12 Parts of silica gel was added to the solution obtained and the resultant mixture was stirred. The mixture was filtered and the filtrate was concentrated to obtain 690 parts of sodium salt of difluorosulfoacetic acid (in which the inorganic salt was contained, purity: 70.9%).

(2) 50.0 Parts of toluene was charged into a mixture of 10.0 parts of sodium salt of difluorosulfoacetic acid (purity: 70.9%), 1.11 parts of ethylene glycol and 6.81 parts of p-toluenesulfonic acid, and the resultant mixture was heated and refluxed for 22 hours. The mixture was concentrated to remove toluene and 104.2 parts of tert-butyl methyl ether was added to the residue obtained. The mixture obtained was stirred and filtered to obtain the solid. To the solid, 96.1 parts of acetonitrile was added and the resultant mixture was stirred and filtered. The filtrate obtained was concentrated to obtain 6.07 parts of the salt represented by the above-mentioned formula (a).

$^1$H-NMR (dimethylsulfoxide-$d_6$, Internal standard: tetramethylsilane): δ (ppm) 4.43 (s, 4H)

(3) 6.07 Parts of the salt represented by the formula (a) obtained in the above-mentioned (2) was mixed with 40.2 parts of chloroform. To the mixture obtained, 60.5 parts of aqueous triphenylsulfoniumchloride solution (concentration: 14.2%) was added and the resultant mixture was stirred for 15 hours. The mixture was separated to obtain the aqueous layer and the organic layer. The aqueous later obtained was extracted with 26.8 parts of chloroform and the chloroform layer obtained was mixed with the organic layer. The organic layer mixed was washed with water and concentrated. 28.7 Parts of ethyl acetate was added to the concentrated liquid obtained and the resultant mixture was stirred and filtered to obtain 8.42 parts of the salt represented by the above-mentioned formula (b) in the form of white solid, which is called as B1.

$^1$H-NMR (dimethylsulfoxide-$d_6$, Internal standard: tetramethylsilane): δ (ppm) 4.42 (s, 4H), 7.74-7.89 (m, 30H)

MS (ESI(+) Spectrum): $M^+$ 263.0 ($C_{18}H_{15}S^+$=263.09)
MS (ESI(−) Spectrum): $M^{2-}$ 376.0 ($C_6H_4F_4O_{10}S_2^{2-}$=375.92)

Salt Synthesis Example 2

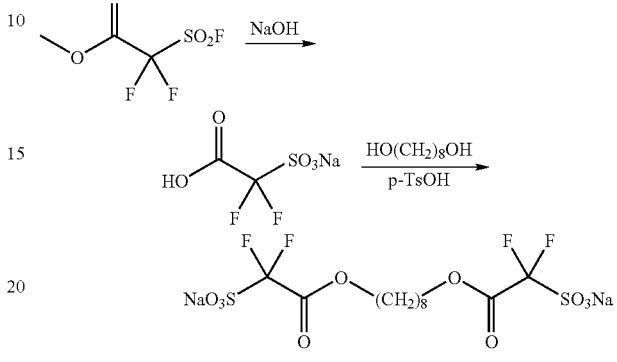

(c)

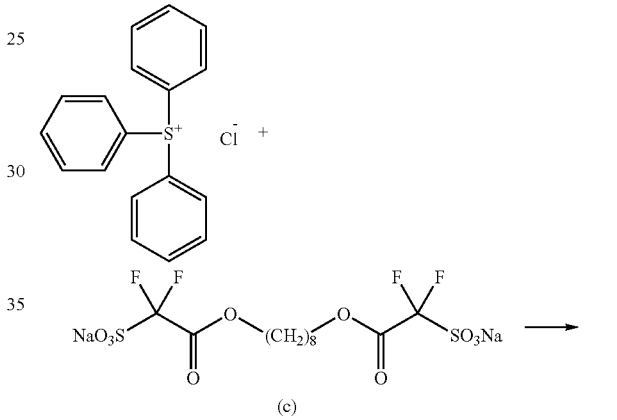

(c)

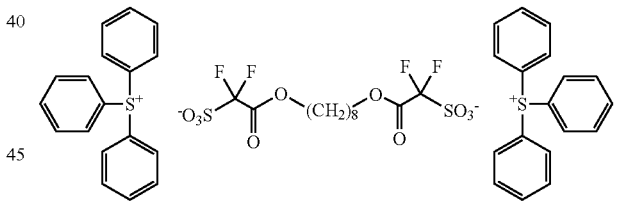

(d)

(1) 1140 Parts of 30% aqueous sodium hydroxide solution was added dropwise into a mixture of 500 parts of methyl difluoro(fluorosulfonyl)acetate and 750 parts of ion-exchanged water in an ice bath. The resultant mixture was stirred at room temperature for 15 hours and then neutralized with 390 parts of conc. hydrochloric acid. 12 Parts of silica gel was added to the solution obtained and the resultant mixture was stirred. The mixture was filtered and the filtrate was concentrated to obtain 690 parts of sodium salt of difluorosulfoacetic acid (in which the inorganic salt was contained, purity: 70.9%).

(2) 50.0 Parts of dichloroethane was charged into a mixture of 10.0 parts of sodium salt of difluorosulfoacetic acid (purity: 70.9%), 2.62 parts of 1,8-octanediol and 6.81 parts of p-toluenesulfonic acid, and the resultant mixture was heated and refluxed for 24 hours. The mixture was concentrated to remove dichloroethane and 93.27 parts of tert-butyl methyl ether was added to the residue obtained. The mixture obtained was stirred and filtered to obtain the solid. To the solid, 96.1 parts of acetonitrile was added and the resultant mixture was stirred and filtered. The filtrate obtained was concentrated to obtain 7.50 parts of the salt represented by the above-mentioned formula (c).

$^1$H-NMR (dimethylsulfoxide-d$_6$, Internal standard: tetramethylsilane): δ (ppm) 1.24 (br, 8H), 1.52-1.59 (m, 4H), 4.16 (t, 4H), 7.74-7.89 (m, 30H)

MS (ESI(+) Spectrum): M$^+$ 263.0 (C$_{18}$H$_{15}$S$^+$=263.09)

MS (ESI(−) Spectrum): M$^{2−}$ 460.0 (C$_{12}$H$_{16}$F$_4$O$_1$S$_2^{2−}$=460.01)

Salt Synthesis Example 3

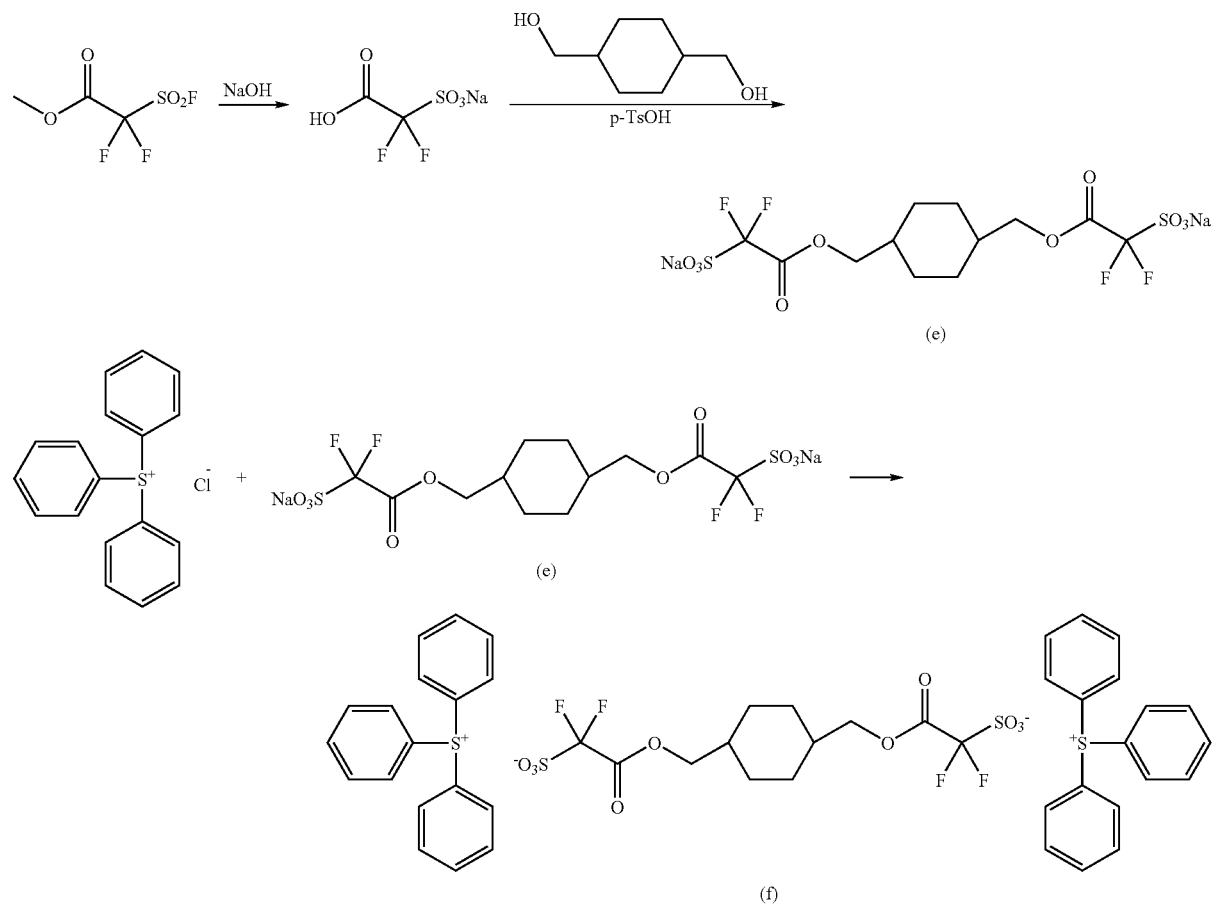

$^1$H-NMR (dimethylsulfoxide-d$_6$, Internal standard: tetramethylsilane): δ (ppm) 1.27 (br, 8H), 1.56-1.61 (m, 4H), 4.17 (t, 4H)

(3) 7.50 Parts of the salt represented by the formula (c) obtained in the above-mentioned (2) was mixed with 63.3 parts of chloroform. To the mixture obtained, 62.4 parts of aqueous triphenylsulfoniumchloride solution (concentration: 14.2%) was added and the resultant mixture was stirred for 15 hours. The mixture was separated to obtain the aqueous layer and the organic layer. The aqueous later obtained was extracted with 42.2 parts of chloroform and the chloroform layer obtained was mixed with the organic layer. The organic layer mixed was washed with water and concentrated. 55.9 Parts of ethyl acetate was added to the concentrated liquid obtained and the resultant mixture was stirred and filtered to obtain 9.89 parts of the salt represented by the above-mentioned formula (d) in the form of white solid, which is called as B2.

(1) 114 Parts of 30% aqueous sodium hydroxide solution was added dropwise into a mixture of 50 parts of methyl difluoro (fluorosulfonyl)acetate and 250 parts of ion-exchanged water in an ice bath. The resultant mixture was stirred at room temperature for 15 hours and then neutralized with 44 parts of conc. hydrochloric acid. The resultant solution was concentrated to obtain 81 parts of sodium salt of difluorosulfoacetic acid (in which the inorganic salt was contained, purity: 63.3%).

(2) 31.4 Parts of dichloroethane was charged into a mixture of 3.95 parts of sodium salt of difluorosulfoacetic acid (purity: 63.3%), 0.55 parts of 1,4-cyclohexanedimethanol and 2.40 parts of p-toluenesulfonic acid, and the resultant mixture was heated and refluxed for 2.5 hours. 0.79 Parts of sodium salt of difluorosulfoacetic acid (purity: 63.3%) was further added to the mixture and the resultant mixture was heated and refluxed for 3 hours. The mixture was concentrated to remove dichloroethane and 100 parts of tert-butyl methyl ether was added to the solid obtained. The resultant mixture was stirred and filtered. To the solid obtained, 100 parts of ethyl acetate was added and the resultant mixture was stirred and filtered. To the solid obtained, 100 parts of methanol was added. The resultant mixture was stirred and filtered. The filtrate obtained was concentrated to obtain 4.32 parts of the salt represented by the above-mentioned formula (e).

$^1$H-NMR (dimethylsulfoxide-$d_6$, Internal standard: tetramethylsilane): δ (ppm) 0.93-1.01 (m, 4H), 1.59 (br, 2H), 1.74 (d, 4H), 4.03 (d, 4H)

(3) 4.32 Parts of the salt represented by the formula (e) obtained in the above-mentioned (2) was mixed with 21.6 parts of methanol. To the mixture obtained, 5.12 parts of triphenylsulfonium chloride, 25.6 parts of methanol and 40 parts of ion-exchanged water were added and the resultant mixture was stirred for 15 hours. The mixture was concentrated to remove methanol. The precipitate was filtered and 50 parts of water was added thereto. The resultant mixture was stirred and filtered to obtain 2.06 parts of the salt represented by the above-mentioned formula (f) in the form of white solid, which is called as B3.

$^1$H-NMR (dimethylsulfoxide-$d_6$, Internal standard: tetramethylsilane): δ (ppm) 0.92-0.99 (m, 4H), 1.58 (br, 2H), 1.74 (d, 4H), 4.02 (d, 4H), 7.75-7.90 (m, 30H)

MS (ESI(+) Spectrum): M$^+$ 263.2 ($C_{18}H_{15}S^+$=263.09)

MS (ESI(−) Spectrum): M$^{2-}$ 458.0 ($C_{12}H_{14}F_4O_{10}S_2^{2-}$=458.00)

Salt Synthesis Example 4

(1) 150 Parts of 2-bromoacetophenone was dissolved in 375 parts of acetone and 66.5 parts of tetrahydrothiophene was added dropwise to the solution obtained. The resultant mixture was stirred at room temperature for 24 hours and the white precipitates were filtered, washed, and dried to obtain 207.9 parts of 1-(2-oxo-2-phenylethyl)tetrahydrothiophenium bromide in the form of white crystals.

$^1$H-NMR (dimethylsulfoxide-$d_6$, Internal standard: tetramethylsilane): δ (ppm) 2.13-2.36 (m, 4H), 3.50-3.67 (m, 4H), 5.41 (s, 2H), 7.63 (t, 2H), 7.78 (t, 1H), 8.02 (d, 2H)

(2) 9.82 Parts of the salt represented by the formula (e) synthesized in a similar manner to the method described in the above-mentioned Salt Synthesis Example 3 (2), was dissolved in 98.2 parts of ion-exchanged water. To the solution obtained, 11.2 parts of 1-(2-oxo-2-phenylethyl)tetrahydrothiophenium bromide obtained in the above-mentioned (1) and 112 parts of methanol were added. The mixture obtained was stirred for 50 hours and concentrated. The residue obtained was extracted twice with 75 parts of chloroform. The middle layer was separated from the upper layer and bottom layer. To the middle layer obtained, 50 parts of ethyl acetate was added and the resultant mixture was stirred. The mixture was filtered to obtain the solid and the solid obtained was mixed with 50 parts of water and the mixture obtained was stirred and filtered to obtain 0.23 part of the salt represented by the above-mentioned formula (g) in the form of white solid, which is called as B4.

$^1$H-NMR (dimethylsulfoxide-$d_6$, Internal standard: tetramethylsilane): δ (ppm) 0.93-1.00 (m, 4H), 1.59 (br, 2H),

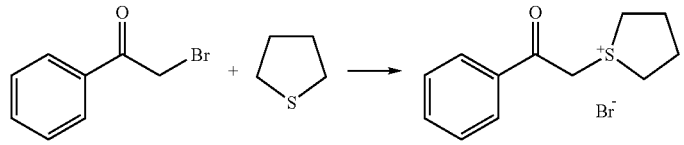

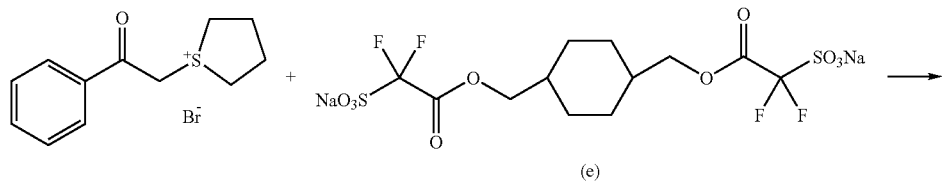

(e)

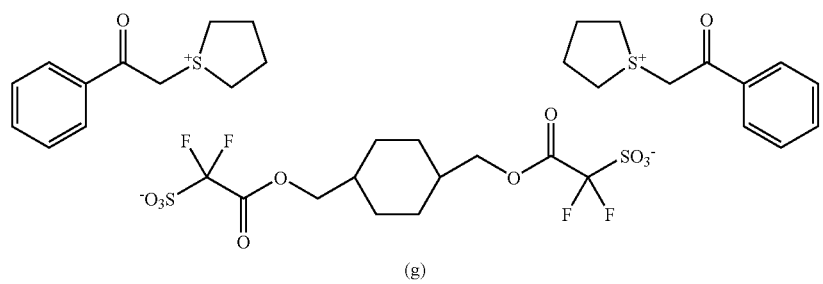

(g)

1.74 (d, 4H), 2.18-2.28 (m, 8H), 3.48-3.62 (m, 8H), 4.03 (d, 4H), 5.31 (s, 4H), 7.63 (t, 4H), 7.78 (t, 2H), 8.01 (d, 4H)

MS (ESI(+) Spectrum): $M^+$ 207.2 ($C_{12}H^{15}OS^+$=207.08)

MS (ESI(-) Spectrum): $M^{2-}$ 458.0 ($C_{12}H_{14}F_4O_{10}S_2^{2-}$=458.00)

Salt Synthesis Example 5

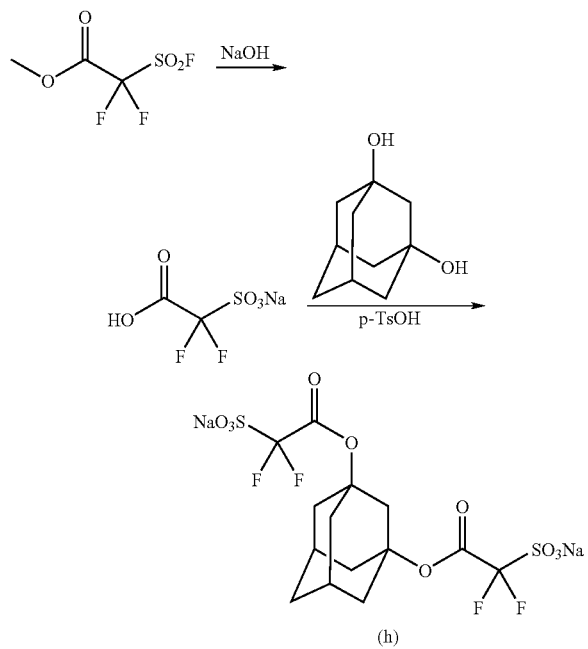

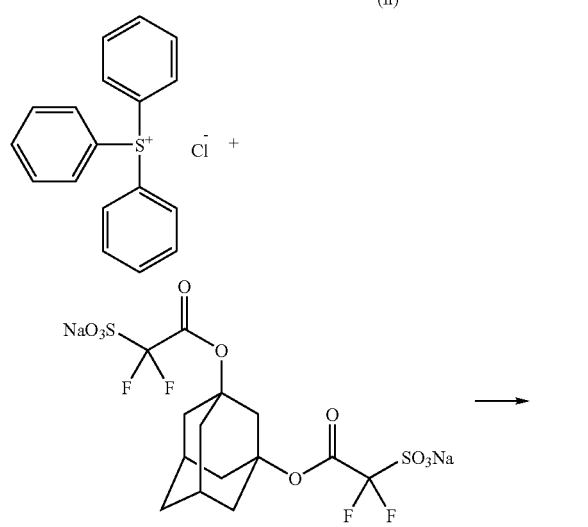

(1) 114 Parts of 30% aqueous sodium hydroxide solution was added dropwise into a mixture of 500 parts of methyl difluoro (fluorosulfonyl)acetate and 750 parts of ion-exchanged water in an ice bath. The resultant mixture was stirred at room temperature for 15 hours and then neutralized with 390 parts of conc. hydrochloric acid. To the resultant solution, 12 parts of silica gel was added and the mixture obtained was stirred and filtered. The filtrate obtained was concentrated to obtain 690 parts of sodium salt of difluorosulfoacetic acid (in which the inorganic salt was contained, purity: 70.9%).

(2) 1.05 Parts of sulfuric acid was added to a mixture of 10.0 parts of sodium salt of difluorosulfoacetic acid (purity: 70.9%), 3.01 parts of 1,3-adamantanediol and 100 parts of monochlorobenzene, and the resultant mixture was heated and refluxed for 3 hours. 0.70 part of sulfuric acid was further added to the mixture and the resultant mixture was heated and refluxed for 21 hours. The mixture was concentrated to remove monochlorobenzene and 57.9 parts of tert-butyl methyl ether was added to the residue obtained. The resultant mixture was stirred and filtered. To the solid obtained, 57.5 parts of acetonitrile was added. The resultant mixture was stirred and filtered. The filtrate obtained was concentrated to obtain 4.25 parts of the salt represented by the above-mentioned formula (h).

$^1$H-NMR (dimethylsulfoxide-d$_6$, Internal standard: tetramethylsilane): δ (ppm) 1.52 (s, 2H), 2.01 (d, 8H), 2.34 (s, 2H), 2.42 (s, 2H)

(3) 4.25 Parts of the salt represented by the formula (h) obtained in the above-mentioned (2) was mixed with 42.5 parts of chloroform. To the mixture obtained, 33.9 parts of aqueous triphenylsulfonium chloride solution (concentration: 14.2%) was added and stirred for 15 hours. The resultant mixture was separated to obtain the organic layer and the water layer. The water layer obtained was extracted with 21.3 parts of chloroform and the chloroform layer obtained and the organic layer were mixed to wash with ion-exchanged water. The solid was precipitated in the organic layer. The organic layer was filtered to obtain 0.66 part of the salt represented by the above-mentioned formula (I) in the form of white solid, which is called as B5.

$^1$H-NMR (dimethylsulfoxide-d$_6$, Internal standard: tetramethylsilane): δ (ppm) 1.50 (s, 2H), 2.00 (d, 8H), 2.32 (s, 2H), 2.41 (s, 2H), 7.74-7.89 (m, 30H)

MS (ESI(+) Spectrum): $M^+$ 263.0 ($C_{18}H_{15}S^+$=263.09)

MS (ESI(-) Spectrum): $M^{2-}$ 482.0 ($C_{14}H_{14}F_4O_{10}S_2^{2-}$=482.00)

Salt Synthesis Example 6

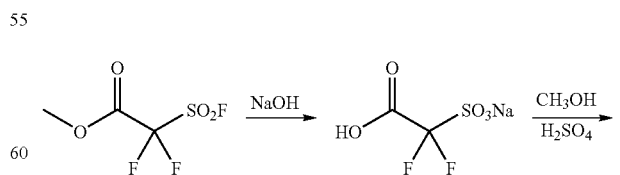

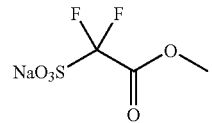

-continued

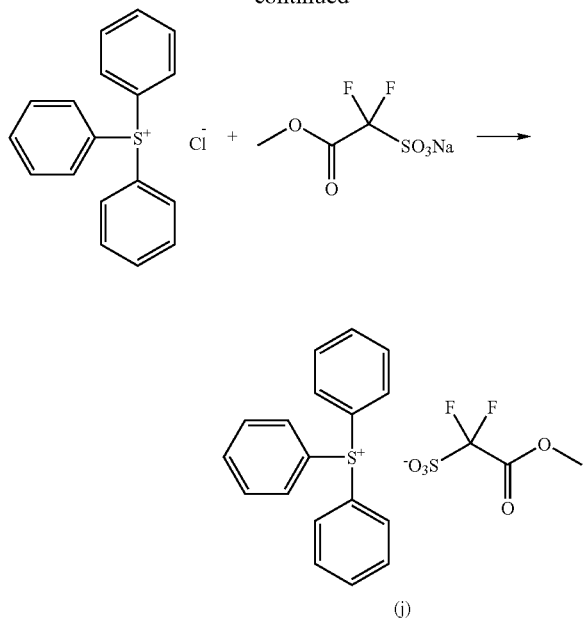

(j)

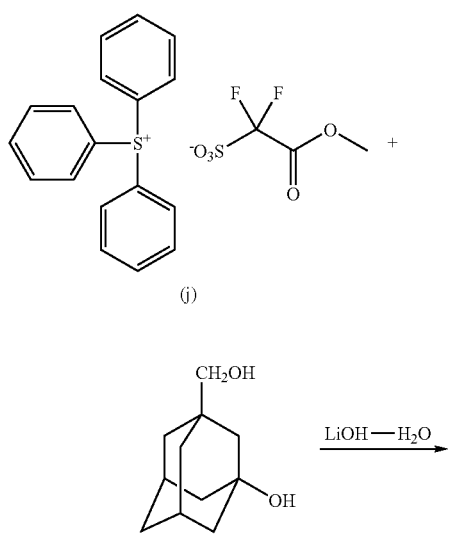

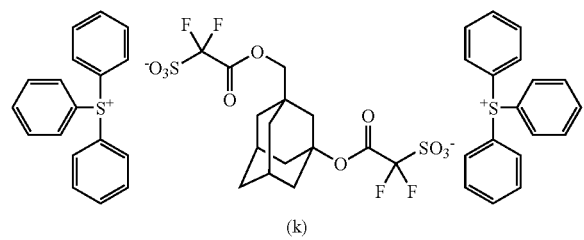

(k)

(1) 1207 Parts of 30% aqueous sodium hydroxide solution was added dropwise into a mixture of 527 parts of methyl difluoro(fluorosulfonyl)acetate and 790 parts of ion-exchanged water in an ice bath. The resultant mixture was stirred at room temperature for 15 hours and then neutralized with 464 parts of conc. hydrochloric acid. The resultant solution was concentrated to obtain 818.3 parts of sodium salt of difluorosulfoacetic acid (in which the inorganic salt was contained, purity: 63.1%).

(2) 600 Parts of methanol was mixed with 120 parts of sodium salt of difluorosulfoacetic acid (purity: 63.1%), and 18.8 parts of sulfuric acid was added thereto. The resultant mixture was heated and refluxed for 24 hours. The mixture was concentrated to remove methanol and 477 parts of n-heptane was added to the residue obtained. The resultant mixture was stirred and filtered. To the solid obtained, 434 parts of acetonitrile was added and the resultant mixture was stirred and filtered. To the solid obtained, 197 parts of acetonitrile was added and the resultant mixture was stirred and filtered. The filtrates obtained were mixed and the mixed filtrate was concentrated to obtain 73.1 parts of sodium salt of difluorosulfoacetic acid.

$^1$H-NMR (dimethylsulfoxide-$d_6$, Internal standard: tetramethylsilane): δ (ppm) 3.77 (s, 3H)

(3) 73.1 Parts of sodium salt of difluorosulfoacetic acid obtained in the above-mentioned (2) was mixed with 292 parts of chloroform. To the mixture obtained, 696 parts of aqueous triphenylsulfonium chloride solution (concentration: 14.8%) was added. The resultant mixture was stirred for 15 hours and separated to the organic layer and the aqueous layer. The aqueous layer was extracted with 146 parts of chloroform and the chloroform layer obtained was mixed with the organic layer. The mixed organic layer was washed with ion-exchanged water and concentrated. 448 parts of tert-butyl methyl ether was added to the residue obtained and the mixture obtained was stirred. The mixture was filtered to obtain 111.0 parts of the salt represented by the above-mentioned formula (j) in the form of white solid.

$^1$H-NMR (dimethylsulfoxide-$d_6$, Internal standard: tetramethylsilane): δ (ppm) 3.76 (s, 3H), 7.75-7.90 (m, 15H)

(4) 2.49 Parts of the salt represented by the formula (j) obtained in the above-mentioned (3), 0.50 part of 3-(hydroxymethyl)adamantan-1-ol, 0.02 part of lithium hydroxide and 24.9 parts of toluene were mixed and the resultant mixture was heated and refluxed at 105° C. for 107 hours. In the middle of heating and refluxing, 1.24 parts of the salt represented by the formula (j) obtained in the above-mentioned (3) and 0.21 part of lithium hydroxide were added thereto. The mixture obtained was concentrated to remove toluene and 57.9 parts of chloroform was added to the residue obtained. The resultant mixture was washed with ion-exchanged water and concentrated. 14.3 parts of ethyl acetate was added to the residue obtained and stirred. Ethyl acetate was removed from the mixture by decantation and 20.2 parts of ethyl acetate was added thereto. The mixture obtained was filtered and the solid obtained was dried to obtain 1.67 parts of the salt represented by the above-mentioned formula (k) in the form of white solid, which is called as B6.

$^1$H-NMR (dimethylsulfoxide-$d_6$, Internal standard: tetramethylsilane): δ (ppm) 1.38-1.58 (m, 6H), 1.85 (s, 2H), 1.99 (dd, 4H), 2.18 (s, 2H), 3.90 (s, 2H), 7.74-7.89 (m, 30H)

MS (ESI(+) Spectrum): M$^+$ 263.2 (C$_{18}$H$_{15}$S$^+$=263.09)

MS (ESI(−) Spectrum): M$^{2-}$ 496.0 (C$_{15}$H$_{16}$F$_4$O$_{10}$S$_2$$^{2-}$=496.01)

Salt Synthesis Example 7

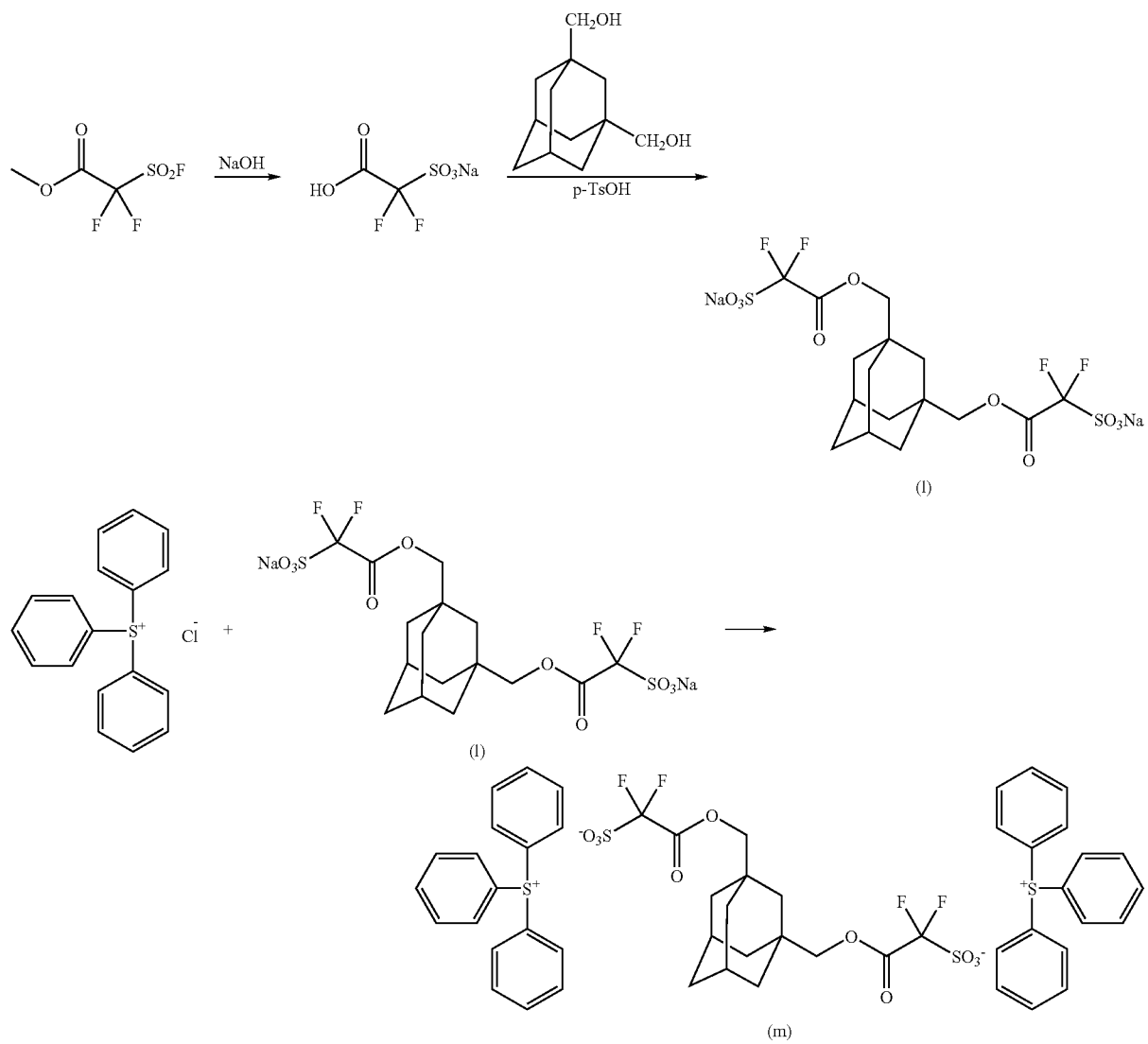

(1) 1140 Parts of 30% aqueous sodium hydroxide solution was added dropwise into a mixture of 500 parts of methyl difluoro(fluorosulfonyl)acetate and 750 parts of ion-exchanged water in an ice bath. The resultant mixture was stirred at room temperature for 15 hours and then neutralized with 390 parts of conc. hydrochloric acid. To the resultant mixture, 12 parts of silica gel was added and the mixture obtained was stirred. The mixture was filtered and the filtrate obtained was concentrated to obtain 690 parts of sodium salt of difluorosulfoacetic acid (in which the inorganic salt was contained, purity: 70.9%).

(2) 50.0 Parts of dichloroethane was added to a mixture of 10.0 parts of sodium salt of difluorosulfoacetic acid (purity: 70.9%), 3.51 parts of 1,3-adamantanedimethanol and 6.81 parts of p-toluenesulfonic acid and the resultant mixture was heated and refluxed for 20 hours. The mixture was concentrated to remove dichloroethane and 96.4 parts of tert-butyl methyl ether was added to the residue obtained. The mixture obtained was stirred and filtered. To the solid obtained, 98.4 parts of acetonitrile was added and the resultant mixture was stirred and filtered. To the solid obtained, 80.5 parts of acetonitrile was added. The filtrates obtained were mixed and the mixed filtrate was concentrated to obtain 9.78 parts of the salt represented by the above-mentioned formula (1).

$^1$H-NMR (dimethylsulfoxide-$d_6$, Internal standard: tetramethylsilane): δ (ppm) 1.28-1.55 (m, 12H), 2.00 (s, 2H), 3.83 (s, 4H)

(3) 9.78 Parts of the salt represented by the formula (1) obtained in the above-mentioned (2) was mixed with 60.7 parts of chloroform. To the mixture obtained, 74.0 parts of aqueous triphenylsulfonium chloride solution (concentration: 14.2%) was added. The resultant mixture was stirred for 15 hours and separated to the organic layer and the aqueous layer. The aqueous layer was extracted with 40.4 parts of chloroform and the chloroform layer obtained was mixed with the organic layer. The mixed organic layer was washed with ion-exchanged water and concentrated. 37.8 Parts of ethyl acetate was added to the residue obtained and the mixture obtained was stirred. The mixture was filtered to obtain 10.52 parts of the salt represented by the above-mentioned formula (m) in the form of white solid, which is called as B7.

$^1$H-NMR (dimethylsulfoxide-$d_6$, Internal standard: tetramethylsilane): δ (ppm) 1.27-1.54 (m, 12H), 1.97 (s, 2H), 3.82 (s, 4H), 7.74-7.89 (m, 30H)

MS (ESI(+) Spectrum): M$^+$ 263.0 ($C_{18}H_{15}S^+$=263.09)

MS (ESI(-) Spectrum): M$^{2-}$ 510.0 ($C_{16}H_{18}F_4O_{10}S_2^{2-}$=510.03)

Salt Synthesis Example 8

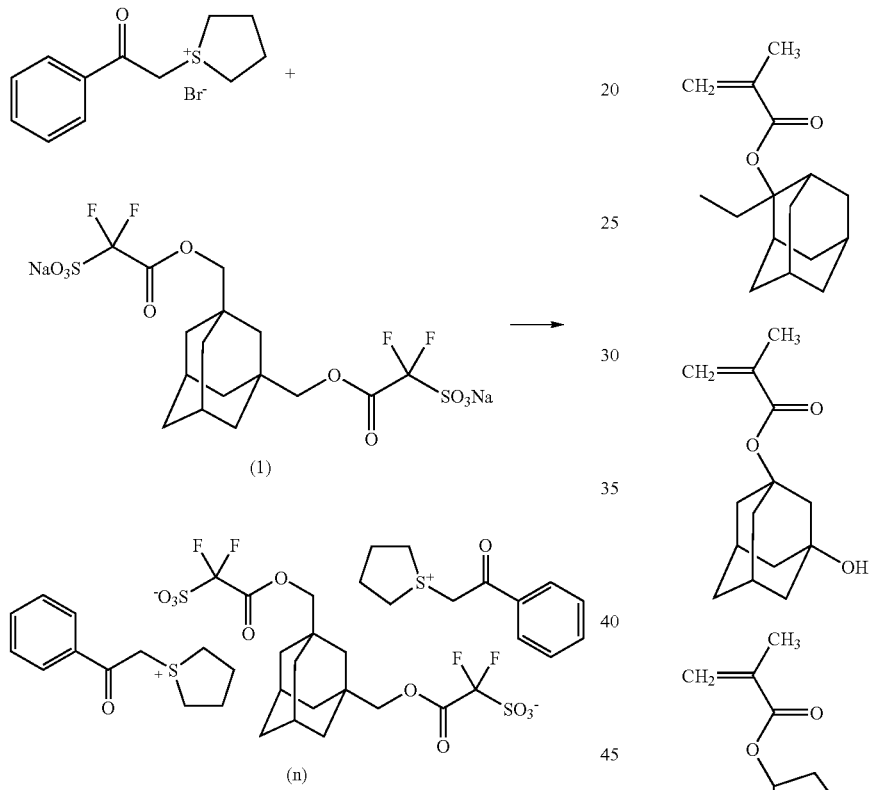

(1)

(n)

7.62 Parts of the salt represented by the formula (1) synthesized in a similar manner to the method described in the above-mentioned Salt Synthesis Example 7 (2), was mixed with 60.7 parts of chloroform. To the mixture obtained, 14.26 parts of 1-(2-oxo-2-phenylethyl)tetrahydrothiophenium bromide obtained in the above-mentioned Salt Synthesis Example 4 (1) and 42.8 parts of ion-exchanged water were added. The resultant mixture was stirred for 15 hours and separated to obtain the organic layer. The organic layer was concentrated. 48.5. Parts of ethyl acetate was added to the residue obtained. The mixture obtained was stirred and filtered to obtain the solid. 70.3 parts of ion-exchanged water was added to the solid obtained. The resultant mixture was stirred and filtrated to obtain the solid. 53.5 Parts of tert-butyl methyl ether was added to the solid obtained. The resultant mixture was stirred and filtrated to obtain 8.33 parts of the salt represented by the above-mentioned formula (n) in the form of white solid, which is called as B8.

$^1$H-NMR (dimethylsulfoxide-$d_6$, Internal standard: tetramethylsilane): δ (ppm) 1.28-1.54 (m, 12H), 1.99 (s, 2H), 2.18-2.29 (m, 8H), 3.46-3.61 (m, 8H), 3.83 (s, 4H), 5.30 (s, 4H), 7.62 (t, 4H), 7.76 (t, 2H), 8.00 (d, 4H)

MS (ESI(+) Spectrum): M$^+$ 207.0 ($C_{12}H_{15}$,OS$^+$=207.08)

MS (ESI(-) Spectrum): M$^{2-}$ 510.0 ($C_{16}H_{18}F_4O_{10}S_2^{2-}$=510.03)

Resin Synthesis Example 1

Monomers used in this Resin Synthesis Example are following monomers M1, M2 and M3.

The monomer M1, monomer M2 and monomer M3 were dissolved in 2 times amount of methyl isobutyl ketone as much as the amount of all monomers to be used (monomer molar ratio; monomer M1: monomer M2: monomer M3=5: 2.5:2.5). To the solution, 2,2'-azobisisobutyronitrile was added as an initiator in a ratio of 2 mol % based on all monomer molar amount, and the resultant mixture was heated at 80° C. for about 8 hours. The reaction solution was poured into large amount of heptane to cause precipitation. The precipitate was isolated and washed twice with large amount of heptane for purification. As a result, copolymer having a weight-average molecular weight of about 9,200 was obtained. This copolymer had the following structural units. This is called as resin R1.

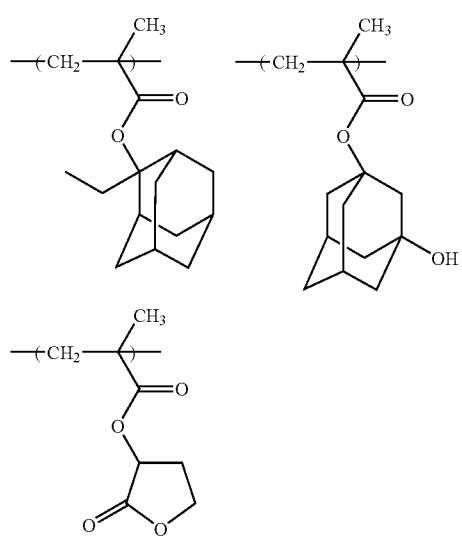
Examples 1 to 3 and Comparative Example 1
Resin
Resin R1
<Acid Generator>
Acid Generator B1:
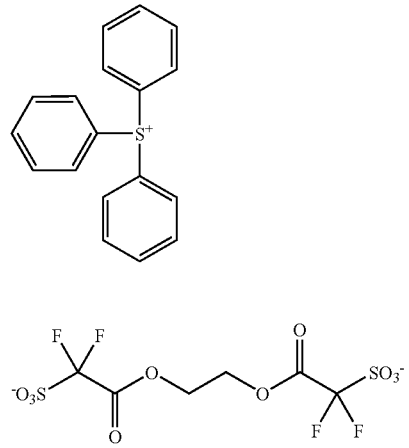
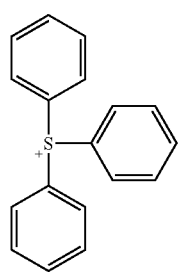
Acid Generator B6:
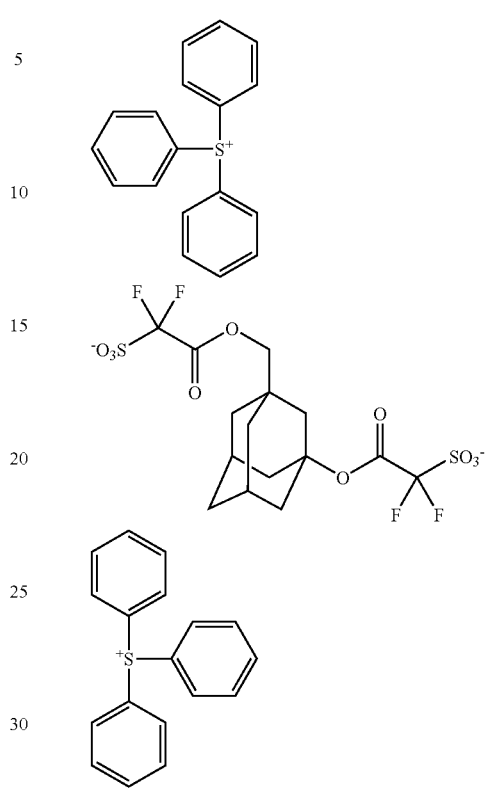
Acid Generator B7:
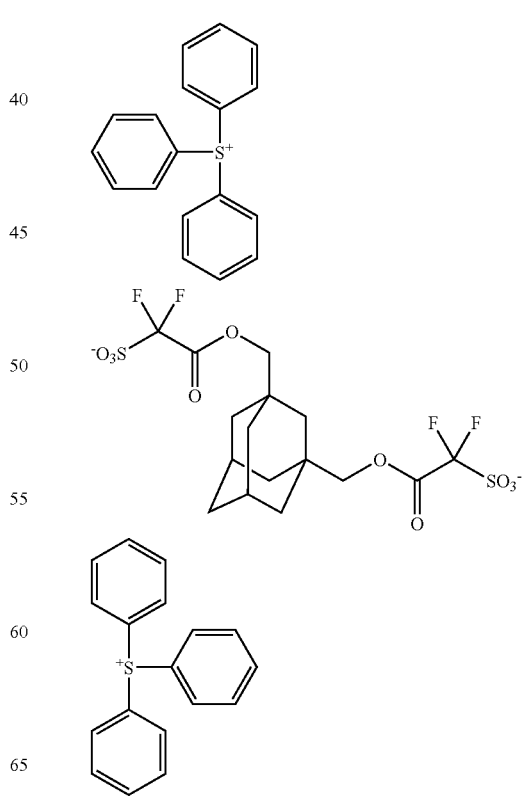

Acid Generator C1: Triphenylsulfonium perfluorobutane-sulfonate

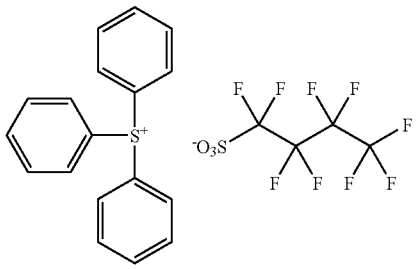

<Quencher>

Quencher Q1: 2,6-diisopropylaniline

<Solvent>

| Solvent Y1: | propylene glycol monomethyl ether acetate | 80.0 parts |
|---|---|---|
| | propylene glycol monomethyl ether | 20.0 parts |
| | γ-butyrolactone | 3.0 parts |

The following components were mixed to give a solution, and the solution was further filtrated through a fluorine resin filter having a pore diameter of 0.2 μm, to prepare resist liquid.

Resin (kind and amount are described in Table 1)
Acid generator (kind and amount are described in Table 1)
Quencher (kind and amount are described in Table 1)
Solvent (kind and amount are described in Table 1)

TABLE 1

| Ex. No. | Resin (kind/amount (part)) | Acid generator (kind/amount (part)) | Quencher (kind/amount (part)) | Solvent |
|---|---|---|---|---|
| Ex. 1 | R1/10 | B1/0.294 | Q1/0.0325 | Y1 |
| Ex. 2 | R1/10 | B6/0.333 | Q1/0.0325 | Y1 |
| Ex. 3 | R1/10 | B7/0.338 | Q1/0.0325 | Y1 |
| Comp. Ex. 1 | R1/10 | C1/0.244 | Q1/0.0325 | Y1 |

Silicon wafers were each coated with "ARC-29A-8", which is an organic anti-reflective coating composition available from Brewer Co., and then baked under the conditions of 215° C. and 60 seconds, to form a 780 Å-thick organic anti-reflective coating. Each of the resist liquids prepared as above was spin-coated over the anti-reflective coating so that the thickness of the resulting film became 0.25 μm after drying. After application of each of the resist liquids, the silicon wafers thus coated with the respective resist liquids were each prebaked on a direct hotplate at a temperature of 130° C. for 60 seconds. Using an ArF excimer stepper ("NSRArF" manufactured by Nikon Corporation, NA=0.55, ⅔ Annular), each wafer on which the respective resist film had been thus formed was exposed to a line and space pattern, while changing stepwise the exposure quantity.

After the exposure, each wafer was subjected to post-exposure baking on a hotplate at a temperature of 130° C. for 60 seconds and then to paddle development for 60 seconds with an aqueous solution of 2.38% tetramethylammonium hydroxide.

Each of a dark field pattern developed on the organic anti-reflective coating substrate after the development was observed with a scanning electron microscope, and the results of which are shown in Table 2. The term "dark field pattern", as used herein, means a pattern obtained by exposure and development through a reticle comprising a chromium base layer (light-shielding layer) and linear glass surface (light-transmitting portion) formed in the chromium base layer and aligned with each other. Thus, the dark field pattern is such that, after exposure and development, resist layer surrounding the line and space pattern remains on substrate.

Effective Sensitivity (ES): It is expressed as the amount of exposure that the line pattern (light-shielding layer) and the space pattern (light-transmitting portion) become 1:1 after exposure through 0.13 μm line and space pattern mask and development.

Resolution: It is expressed as the minimum size of space pattern which gave the space pattern split by the line pattern at the exposure amount of the effective sensitivity.

Profile T/B: It is expressed by a ratio of top side length (referred to as T) and bottom side length (referred to as B) in line part of 0.13 μm line and space pattern. The closer to 1 the ratio is, the better the profile of its resist pattern is.

TABLE 2

| Ex. No. | ES (mJ/cm$^2$) | Resolution (μm) | Profile T/B |
|---|---|---|---|
| Ex. 1 | 50.0 | 0.12 | 0.83 |
| Ex. 2 | 52.5 | 0.12 | 0.91 |
| Ex. 3 | 50.0 | 0.125 | 1.00 |
| Comp. Ex. 1 | 52.5 | 0.13 | 0.62 |

Apparent from the results shown in Table 2, while keeping equivalent effective sensitivity, resist pattern obtained by Examples 1 to 3 have excellent pattern shape because Profile T/B of Examples 1 to 3 are closer to 1 than that of Comparative Example 1.

The salt represented by the formula (I) is suitably used for an acid generator capable of providing chemically amplified positive resist compositions giving patterns having higher resolution and excellent pattern shape, and the present resist composition is especially suitable for ArF excimer laser lithography, KrF excimer laser lithography and ArF immersion lithography.

What is claimed is:

1. A salt represented by the formula (I):

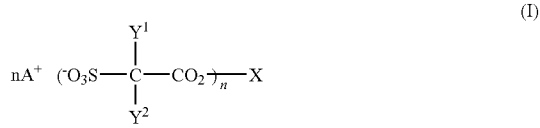

wherein X represents an n-valent connecting group, $Y^1$ and $Y^2$ each independently represent a fluorine atom or a C1-C6 perfluoroalkyl group, n represents 2 or 3, and $A^+$ represents an organic counter ion.

2. The salt according to claim 1, wherein $Y^1$ and $Y^2$ each independently represent a fluorine atom or a trifluoromethyl group.

3. The salt according to claim 1, wherein n is 2.

4. The salt according to claim 1, wherein the organic counter ion is at least one cation selected from a cation represented by the formula (IIa):

(IIa)

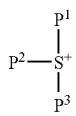

wherein P¹, P² and P³ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

(IIb)

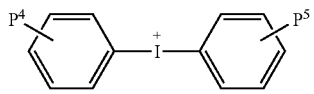

wherein P⁴ and P⁵ each independently represent a hydrogen atom, a hydroxyl group, a C1-C12 alkyl group or a C1-C12 alkoxy group, and a cation represented by the formula (IIc):

(IIc)

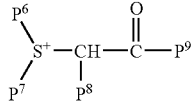

wherein P⁶ and P⁷ each independently represent a C1-C12 alkyl group or a C3-C12 cycloalkyl group, or P⁶ and P⁷ are bonded to form a C3-C12 divalent acyclic hydrocarbon group which forms a ring together with the adjacent S⁺, and at least one —CH₂— in the divalent acyclic hydrocarbon group is optionally replaced with —CO—, —O— or —S—, P⁸ represents a hydrogen atom, P⁹ represents a C1-C12 alkyl group, a C3-C12 cycloalkyl group or an aromatic group which may be substituted, or P⁸ and P⁹ are bonded to form a divalent acyclic hydrocarbon group which forms a 2-oxocycloalkyl group together with the adjacent —CHCO—, and at least one —CH₂— in the divalent acyclic hydrocarbon group may be replaced with —CO—, —O— or —S—.

5. The salt according to claim 1, wherein the organic counter ion is a cation represented by the formula (IId):

(IId)

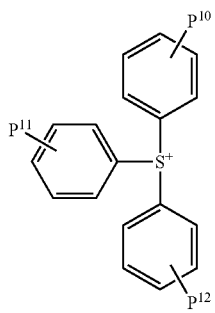

wherein P¹⁰, P¹¹ and P¹² each independently represent a hydrogen atom or a C1-C4 alkyl group.

6. The salt according to claim 1, wherein the n-valent connecting group is a C1-C30 n-valent hydrocarbon group which may be substituted with at least one selected from a C1-C6 alkoxy group, a C1-C4 perfluoroalkyl group, a C1-C6 hydroxyalkyl group, a hydroxyl group and a cyano group, and at least one —CH₂— in the C1-C30 n-valent hydrocarbon group may be replaced with —O— or —CO—.

7. The salt according to claim 1, wherein the salt represented by the formula (I) is a salt represented by the formula (IIIa), (IIIb) or (IIIc);

(IIIa)

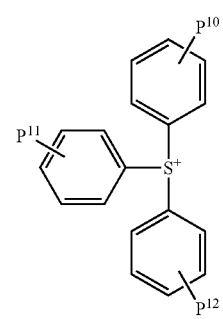

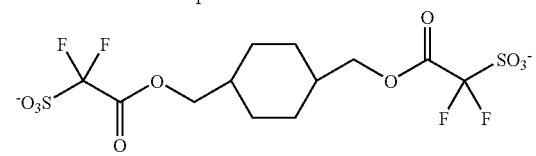

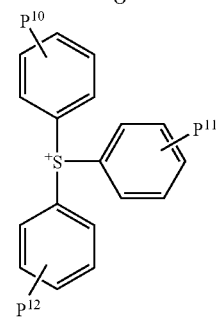

(IIIb)

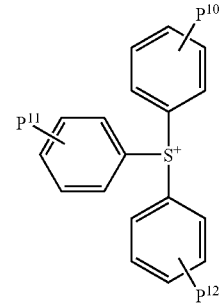

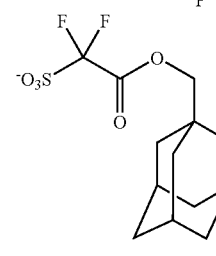

-continued

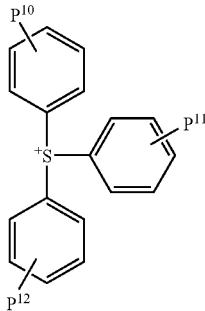

(IIIc)

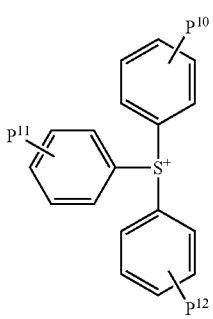

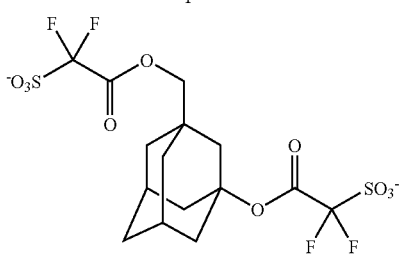

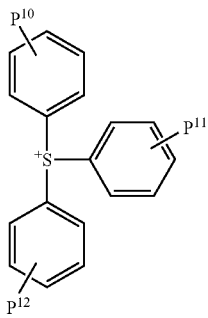

wherein $P^{10}$, $P^{11}$ and $P^{12}$ are the same as defined in claim 5.

8. A salt represented by the formula (IV):

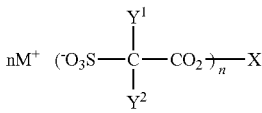
(IV)

wherein X represents an n-valent connecting group, $Y^1$ and $Y^2$ each independently represent a fluorine atom or a C1-C6 perfluoroalkyl group, n represents 2 or 3, and M represents Li, Na, K or Ag.

9. A process for production of a salt represented by the formula (IV):

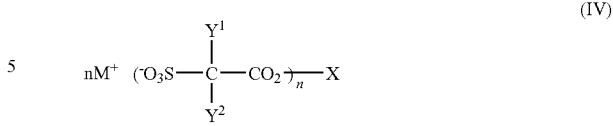
(IV)

wherein X represents an n-valent connecting group, $Y^1$ and $Y^2$ each independently represent a fluorine atom or a C1-C6 perfluoroalkyl group, n represents 2 or 3, and M represents Li, Na, K or Ag, which comprises reacting a compound represented by the formula (V):

$$(HO)_n X \quad (V)$$

wherein X and n are the same as the defined above, with a salt represented by the formula (VI):

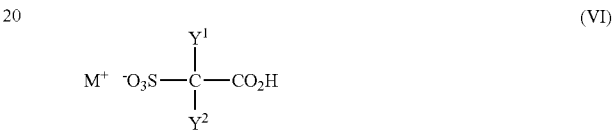
(VI)

wherein $Y^1$, $Y^2$ and M are the same as defined above.

10. A process for production of a salt represented by the formula (IV):

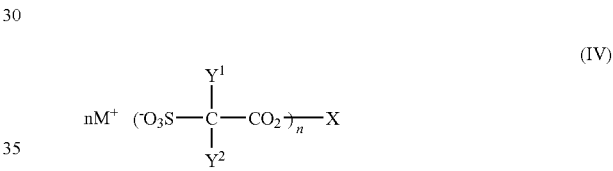
(IV)

wherein X represents an n-valent connecting group, $Y^1$ and $Y^2$ each independently represent a fluorine atom or a C1-C6 perfluoroalkyl group, n represents 2 or 3, and M represents Li, Na, K or Ag, which comprises reacting a compound represented by the formula (V):

$$(HO)_n X \quad (V)$$

wherein X and n are the same as the defined above, with a salt represented by the formula (VII):

(VII)

wherein $Y^1$, $Y^2$ and M are the same as defined above and Q represents a C1-C4 alkyl group.

11. A process for production of a salt represented by the formula (I):

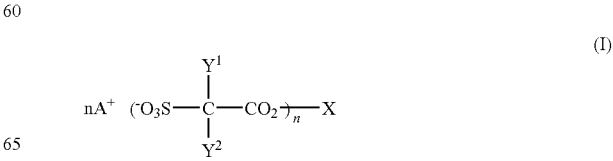
(I)

wherein X represents an n-valent connecting group, $Y^1$ and $Y^2$ each independently represent a fluorine atom or a C1-C6 perfluoroalkyl group, n represents 2 or 3, and $A^+$ represents an organic counter ion, which comprises reacting a salt represented by the formula (IV):

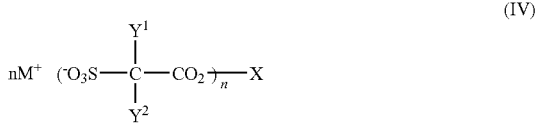

(IV)

wherein X, $Y^1$, $Y^2$ and n are the same as defined above, and M represents Li, Na, K or Ag, with a compound represented by the formula (VIII):

$$A^+Z^- \quad \text{(VIII)}$$

wherein $A^+$ is the same as defined above and Z represents F, Cl, Br, I, $BF_4$, $AsF_6$, $SbF_6$, $PF_6$ or $ClO_4$.

12. A process for production of a salt represented by the formula (I):

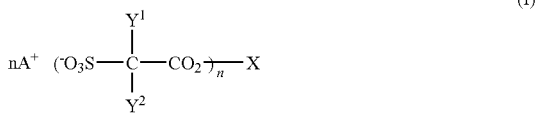

(I)

wherein X represents an n-valent connecting group, $Y^1$ and $Y^2$ each independently represent a fluorine atom or a C1-C6 perfluoroalkyl group, n represents 2 or 3, and $A^+$ represents an organic counter ion, which comprises reacting a compound represented by the formula (V):

$$(HO)_n X \quad \text{(V)}$$

wherein X and n are the same as the defined above, with a salt represented by the formula (IX):

(IX)

wherein $A^+$, $Y^1$ and $Y^2$ are the same as defined above and Q represents a C1-C4 alkyl group.

13. A chemically amplified positive resist composition comprising a salt represented by the formula (I):

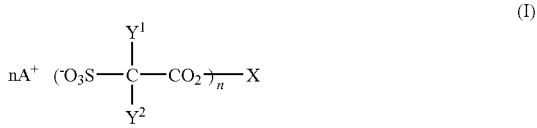

(I)

wherein X represents an n-valent connecting group, $Y^1$ and $Y^2$ each independently represent a fluorine atom or a C1-C6 perfluoroalkyl group, n represents 2 or 3, and $A^+$ represents an organic counter ion, and a resin which contains a structural unit which has an acid-labile group and which itself is insoluble or poorly soluble in an aqueous alkali solution but becomes soluble in an aqueous alkali solution by the action of an acid.

14. The chemically amplified positive resist composition according to claim 13, wherein $Y^1$ and $Y^2$ each independently represent a fluorine atom or a trifluoromethyl group.

15. The chemically amplified positive resist composition according to claim 13, wherein n is 2.

16. The chemically amplified positive resist composition according to claim 13, wherein the organic counter ion is at least one cation selected from a cation represented by the formula (IIa):

(IIa)

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

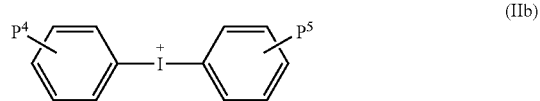

(IIb)

wherein $P^4$ and $P^5$ each independently represent a hydrogen atom, a hydroxyl group, a C1-C12 alkyl group or a C1-C12 alkoxy group, and a cation represented by the formula (IIc):

(IIc)

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —$CH_2$— in the divalent acyclic hydrocarbon group may be replaced with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ are bonded to form a divalent acyclic hydrocarbon group which forms a 2-oxocycloalkyl group together with the adjacent —CHCO—, and at least one —$CH_2$— in the divalent acyclic hydrocarbon group may be replaced with —CO—, —O— or —S—.

17. The chemically amplified positive resist composition according to claim 13, wherein the organic counter ion is a cation represented by the formula (IId):

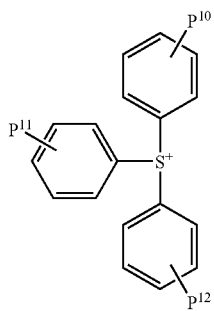
(IId)

wherein P¹⁰, P¹¹ and P¹² each independently represent a hydrogen atom or a C1-C4 alkyl group.

18. The chemically amplified positive resist composition according to claim 13, wherein the n-valent connecting group is a C1-C30 n-valent hydrocarbon group which may be substituted with at least one selected from a C1-C6 alkoxy group, a C1-C4 perfluoroalkyl group, a C1-C6 hydroxyalkyl group, a hydroxyl group and a cyano group, and at least one —CH₂— in the C1-C30 n-valent hydrocarbon group may be replaced with —O— or —CO—.

19. The chemically amplified positive resist composition according to claim 13, wherein the salt of the formula (I) is a salt represented by the formula (IIIa), (IIIb) or (IIIc);

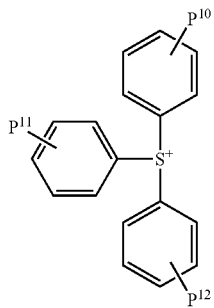
(IIIa)

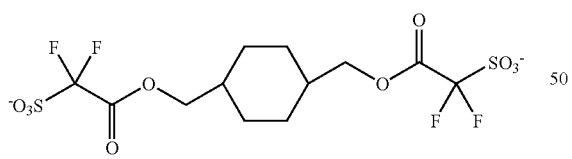

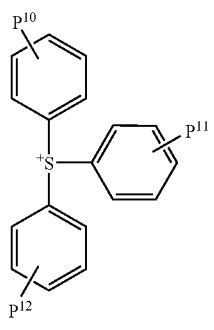

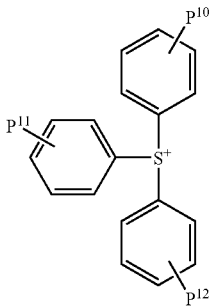
(IIIb)

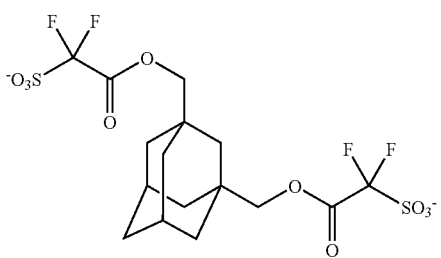

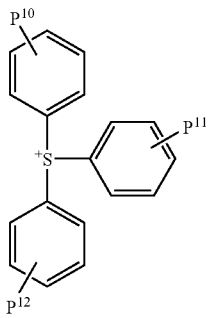

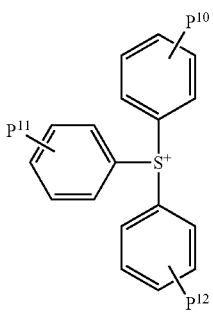
(IIIc)

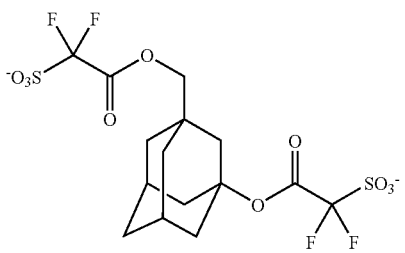

-continued

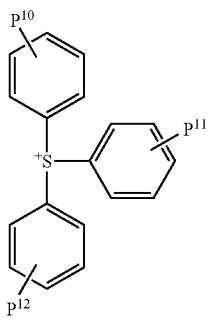

wherein $P^{10}$, $P^{11}$ and $P^{12}$ are the same as defined in claim 17.

20. The chemically amplified positive resist composition according to claim 13, the resin contains a structural unit derived from a monomer having a bulky and acid-labile group.

21. The chemically amplified positive resist composition according to claim 20, the bulky and acid-labile group is a 2-alkyl-2-adamantyl ester group or a 1-(1-adamantyl)-1-alkylalkyl ester group.

22. The chemically amplified positive resist composition according to claim 20, the monomer having a bulky and acid-labile group is 2-alkyl-2-adamantyl acrylate, 2-alkyl-2-adamantyl methacrylate, 1-(1-adamantyl)-1-alkylalkyl acrylate, 1-(1-adamantyl)-1-alkylalkyl methacrylate, 2-alkyl-2-adamantyl 5-norbornene-2-carboxylate, 1-(1-adamantyl)-1-alkylalkyl 5-norbornene-2-carboxylate, 2-alkyl-2-adamantyl α-chloroacrylate or 1-(1-adamantyl)-1-alkylalkyl α-chloroacrylate.

23. The chemically amplified positive resist composition according to claim 20, the monomer having a bulky and acid-labile group is a 2-alkyl-2-adamantyl acrylate, a 2-alkyl-2-adamantyl methacrylate, a 2-alkyl-2-adamantyl α-chloroacrylate or a 1-(1-adamantyl)-1-alkylalkyl α-chloroacrylate.

24. The chemically amplified positive resist composition according to claim 20, the monomer having a bulky and acid-labile group is a 2-alkyl-2-adamantyl acrylate or a 2-alkyl-2-adamantyl methacrylate.

25. The chemically amplified positive resist composition according to claim 20, the monomer having a bulky and acid-labile group is 2-ethyl-2-adamantyl acrylate, 2-ethyl-2-adamantyl methacrylate, 2-isopropyl-2-adamantyl acrylate or 2-isopropyl-2-adamantyl methacrylate.

26. The chemically amplified positive resist composition according to claim 20, the resin contains a structural unit derived from a monomer having an acid-stable group, in addition to the structural unit derived from a monomer having a bulky and acid-labile group.

27. The chemically amplified positive resist composition according to claim 26, the structural unit derived from the monomer having an acid-stable group is a structural unit derived from 3-hydroxy-1-adamantyl acrylate;
a structural unit derived from 3-hydroxy-1-adamantyl methacrylate;
a structural unit derived from 3,5-dihydroxy-1-adamantyl acrylate;
a structural unit derived from 3,5-dihydroxy-1-adamantyl methacrylate;
a structural unit derived from α-acryloyloxy-γ-butyrolactone;
a structural unit derived from α-methacryloyloxy-γ-butyrolactone;
a structural unit derived from β-acryloyloxy-γ-butyrolactone;
a structural unit derived from β-methacryloyloxy-γ-butyrolactone;
a structural unit represented by the formula (X):

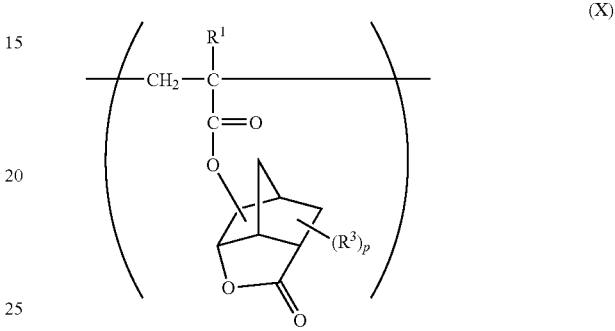

wherein $R^1$ represents a hydrogen atom or a methyl group, $R^3$ represents a methyl group, a trifluoromethyl group or a halogen atom, p represents an integer of 0 to 3, and when p represents 2 or 3, $R^3$s may be the same or different each other;
a structural unit represented by the formula (XI):

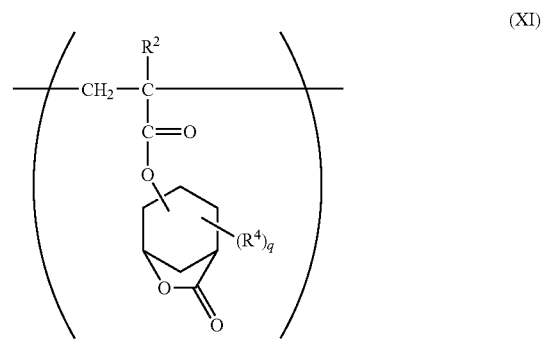

wherein $R^2$ represents a hydrogen atom or a methyl group, $R^4$ represents a methyl group, a trifluoromethyl group or a halogen atom, q represents an integer of 0 to 3, and when q represents 2 or 3, $R^4$s may be the same or different each other;
a structural unit derived from p-hydroxystyrene;
a structural unit derived from m-hydroxystyrene;
a structural unit represented by the formula (XII):

wherein $R^5$ and $R^4$ each independently represents a hydrogen atom, a C1-C3 alkyl group, a C1-C3 hydroxyalkyl group, a carboxyl group, a cyano group or a —COOU group in which U represents an alcohol residue, or $R^5$ and $R^6$ can be bonded together to form a carboxylic anhydride residue represented by —C(=O)OC(=O)—;

a structural unit represented by the formula (XIII):

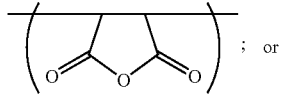

(XIII)

; or a structural unit represented by the formula (XIV):

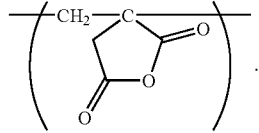

(XIV)

.

28. The chemically amplified positive resist composition according to claim 13, wherein the chemically amplified positive resist composition further comprises a basic compound.

* * * * *